United States Patent [19]
Davis et al.

[11] Patent Number: 6,146,831
[45] Date of Patent: Nov. 14, 2000

[54] CELLULAR MODELS FOR DIABETES AND OTHER DISEASES ASSOCIATED WITH MITOCHONDRIAL DEFECTS

[75] Inventors: Robert E. Davis; Corinna Herrnstadt, both of San Diego, Calif.

[73] Assignee: Mitokor, San Diego, Calif.

[21] Appl. No.: 09/200,419

[22] Filed: Nov. 23, 1998

Related U.S. Application Data

[60] Division of application No. 08/732,564, Oct. 21, 1996, Pat. No. 5,840,493, which is a continuation-in-part of application No. 08/414,969, Mar. 31, 1995, abandoned, which is a continuation-in-part of application No. 08/219,842, Mar. 30, 1994, Pat. No. 5,565,323, which is a continuation-in-part of application No. 08/397,808, Mar. 3, 1995, Pat. No. 5,888,498.

[51] Int. Cl.⁷ .............................. C12Q 1/68; C12P 21/04; C12P 1/02; C12N 5/08
[52] U.S. Cl. ...................... 435/6; 435/70.2; 435/172.2; 435/366
[58] Field of Search ........................... 435/6, 70.2, 172.2, 435/366

[56] References Cited

PUBLICATIONS

Chomyn et al., "In Vitro Genetic Transfer of Protein Synthesis and Respiration Defects to Mitochondrial DNA–Less Cells with Myopathy–Patient Mitochondria", Molecular and Cellular Biology, vol. 11(4), pp. 2236–2244, Apr. 1991.

Soejima et al., "Mitochondrial DNA is required for Regulation of Glucose–stimulated Insulin secretion in a Mouse Pancreatic Beta Cell Line, MIN6", The Journal of Biological Chemistry, vol. 271 (42), pp. 26194–26199, Oct. 1996.

*Primary Examiner*—Jeffrey Fredman
*Assistant Examiner*—Arun Chakrabarti
*Attorney, Agent, or Firm*—Seed Intellectual Property Law Group PLLC

[57] ABSTRACT

The present invention relates to genetic mutations in mitochondrial genes that segregate with diabetes mellitus. The invention provides methods for detecting such mutations, as a diagnostic for diabetes mellitus, either before or after the onset of clinical symptoms. Examples of specific mutations in the mitochondrial ATP synthase 8/6 gene and tRNA lysine gene are given. The invention also provides treatments for dysfunctions due to mitochondrial genes that segregate with diabetes mellitus. Cybrid cell lines are described which are useful as model systems for the study of the mitochondrial metabolic disorders that are associated with diabetes mellitus, and for identifying therapeutic compounds and treatments for this disease.

6 Claims, 5 Drawing Sheets

```
                        SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
         (A) LENGTH: 23 base pairs
         (B) TYPE: nucleic acid
         (C) STRANDEDNESS: double
         (D) TOPOLOGY: linear (ii) MOLECULE TYPE: genomic (xi) SEQUENCE DESCRIPTION: SEQ ID NO:1:

GCCCACTGTA AAGCTAACTT AGC                                              23

(2) INFORMATION FOR SEQ ID NO:2:

(i) SEQUENCE CHARACTERISTICS:
         (A) LENGTH: 22 base pairs
         (B) TYPE: nucleic acid
         (C) STRANDEDNESS: double
         (D) TOPOLOGY: linear (ii) MOLECULE TYPE: genomic (xi) SEQUENCE DESCRIPTION: SEQ ID NO:2:

TAGTCGGTTG TTGATGAGAT AT                                               22

(2) INFORMATION FOR SEQ ID NO:3:

(i) SEQUENCE CHARACTERISTICS:
         (A) LENGTH: 23 base pairs
         (B) TYPE: nucleic acid
         (C) STRANDEDNESS: double
         (D) TOPOLOGY: linear (ii) MOLECULE TYPE: genomic (xi) SEQUENCE DESCRIPTION: SEQ ID NO:3:

CGTCTTGCAC TCATGAGTTG TCC                                              23

(2) INFORMATION FOR SEQ ID NO:4:

(i) SEQUENCE CHARACTERISTICS:
```

```
        (A) LENGTH: 25 base pairs
        (B) TYPE: nucleic acid
        (C) STRANDEDNESS: double
        (D) TOPOLOGY: linear (ii) MOLECULE TYPE: genomic (xi) SEQUENCE DESCRIPTION: SEQ ID NO:4:

ATTTTCGTTC ATTTTGGTTC TCAGG                                            25

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: genomic (xi) SEQUENCE DESCRIPTION: SEQ ID NO:5:

TAGCATTAAC CTTTTAAGTT AAAGA                                            25

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: genomic (xi) SEQUENCE DESCRIPTION: SEQ ID NO:6:

TCGTTCATTT TGGTTCTCA                                                   19
```

CELLULAR MODELS FOR DIABETES AND OTHER DISEASES ASSOCIATED WITH MITOCHONDRIAL DEFECTS

CROSS-REFERENCE TO RELATED APPLICATION

This application is a Divisional of U.S. patent application Ser. No. 08/734,564, filed Oct. 21, 1996 which is now U.S. Pat. No. 5,840,493.

This application is a continuation-in-part application of application Ser. No. 08/414,969, filed Mar. 31, 1995, now abandoned which is a continuation-in-part of application Ser. No. 08/219,842 filed on Mar. 30, 1994, now U.S. Pat. No. 5,565,323, for DIAGNOSTIC AND THERAPEUTIC COMPOSITIONS FOR ALZHEIMER'S DISEASE, and of application Ser. No. 08/397,808, filed on Mar. 3, 1995, now U.S. Pat. No. 5,888,498 for CELLULAR AND ANIMAL MODELS FOR DISEASES ASSOCIATED WITH MITOCHONDRIAL DEFECTS, which are hereby incorporated by reference.

FIELD OF THE INVENTION

The present invention relates generally to model systems for diseases that involve defects in the function of mitochondria, where those defects arise from defects in the genes of those mitochondria. The invention also relates to the use of these model systems for screening drugs and evaluating the efficacy of treatments for those diseases. In particular, the invention relates to the diagnosis and treatment of late onset diabetes mellitus and related pathologies, such as impaired glucose tolerance and insulin dependent or non-insulin dependent diabetes.

BACKGROUND OF THE INVENTION

Diabetes mellitus is a common degenerative disease affecting 5 to 10 percent of the population in developed countries. It is a heterogenous disorder with a strong genetic component; monozygotic twins are highly concordant and there is a high incidence of the disease among first degree relatives of affected individuals. The propensity for developing diabetes mellitus is reportedly maternally inherited, suggesting a mitochondrial genetic involvement. Alcolado, J. C. and Alcolado, R., *Br. Med. J.* 302: 1178–1180 (1991); Reny., S. L., *International J. Epidem.* 23: 886–890 (1994).

Studies have shown that diabetes mellitus may be preceded by or associated with certain related disorders. For example, it is estimated that forty million individuals in the U.S. suffer from late onset impaired glucose tolerance (IGT). IGT patients fail to respond to glucose with increased insulin secretion. A small percentage of IGT individuals (5–10%) progress to insulin deficient non-insulin dependent diabetes (NIDDM) each year. Some of these individuals further progress to insulin dependent diabetes mellitus (IDDM). This form of NIDDM or IDDM is associated with decreased release of insulin by pancreatic beta cells and/or a decreased end-organ response to insulin. Other symptoms of diabetes mellitus and conditions that precede or are associated with diabetes mellitus include: obesity, vascular pathologies, peripheral and sensory neuropathies, blindness, and deafness.

Due to the strong genetic component of diabetes mellitus, the nuclear genome has been the main focus of the search for causative genetic mutations. However, despite intense effort, nuclear genes that segregate with diabetes mellitus are known only for rare mutations in the insulin gene, the insulin receptor gene, the adenosine deaminase gene and the glucokinase gene.

The maternal heredity associated with diabetes mellitus suggests that mitochondrial inheritance might play a role, since mitochondrial genes are maternally inherited. Indeed, a rare form of late-onset NIDDM associated with nerve deafness appears to segregate with a point mutation in a mitochondrial tRNA gene ($tRNA^{leu}$). Individuals carrying this mutation often present with impaired insulin secretion in response to glucose and are usually given the diagnosis of insulin dependent diabetes mellitus (IDDM), slowly progressive IDDM, or insulin deficient non-insulin dependent diabetes (NIDDM). Although this mutation accounts for less than 1% of NIDDM cases, it raises the possibility that other mutations in mtDNA may associate with NIDDM.

Mitochondrial DNA (mtDNA) is a small circular DNA that is approximately 17 Kb long in humans. The mtDNA encodes for two ribosomal RNAs (rRNA), a complete set of transfer RNAs (tRNA), and thirteen proteins, including two ATP synthase genes, ATP synthase subunits 6 and 8.

Most of the mtDNA present in an individual is maternally derived from the mtDNA contained within the ovum at the time of the individual's conception. Mutations in mtDNA sequences that affect all copies of mtDNA in an individual are known as homoplasmic. Mutations which affect only some copies of mtDNA are known as heteroplasmic and will vary between different mitochondria in the same individual.

Despite indications of a possible mitochondrial etiology for at least some forms of diabetes mellitus, neither the incidence nor the exact mechanism producing mitochondrial transport dysfunction in late onset diabetes is known, nor has a genetic or structural basis for these dysfunctions been identified. Without knowing what causes these electron transport dysfunctions and in particular the genetic or structural basis, it is difficult to diagnose or treat late onset diabetes.

Clearly then, a reliable diagnosis of late onset diabetes at its earliest stages is critical for efficient and effective intercession and treatment of this debilitating disease. There is a need for a non-invasive diagnostic assay that is reliable at or before the earliest manifestations of late onset diabetes symptoms. There is also a need for developing therapeutic regimens or drugs for treating both the symptoms of diabetes mellitus and the disease itself.

However, the identification of diagnostic assays and of therapeutic regimens or drugs that are useful in the treatment of disorders associated with mitochondrial defects has historically been hampered by the lack of reliable model systems that could be used in rapid and informative screening. Animal models do not exist for many of the diseases that are associated with mitochondrial gene defects. Appropriate cell culture model systems are either not available, or are difficult to establish and maintain. Furthermore, even when cell culture models are available, it is often not possible to discern whether the mitochondrial or the nuclear genome is responsible for a given phenotype, as mitochondrial functions are often encoded by both nuclear and mitochondrial genes. It is, therefore, also not possible to tell whether the apparent effect of a given drug or treatment operates at the level of the mitochondrial genome or elsewhere.

One approach that has been useful in discerning which genome is responsible is to eliminate the mitochondrial DNA in cultured cells known to have proper mitochondrial function and then transfer to such cells the mitochondria from diseased patients. However, the resulting cell lines, called $\rho°$ cell lines, tend to be unstable and hard to culture. Fully differentiated cell lines are used as the targets for transplantation, but their naturally limited life spans makes them particularly unsuitable for screening purposes. In addition, such transformations have not been done using cells of the type that are most affected by the disease, making it unclear whether the mitochondrial deficiencies observed in the transformants are related to the disease state being studied.

The present invention satisfies these needs for a useful diagnostic and effective treatment of late onset diabetes and provides related advantages, as well.

SUMMARY OF THE INVENTION

The present invention relates to the identification of genetic mutations in mitochondrial genes, which segregate with late onset diabetes. The invention provides methods for detecting such mutations as a diagnostic for late onset diabetes, either before or after the onset of clinical symptoms. More specifically, the present invention provides a method for detecting the presence or risk of late onset diabetes by obtaining a biological sample containing mitochondria from a subject and determining the presence of at least one mutation in the sequence of a mitochondrial ATP synthase gene or mitochondrial tRNA lysine gene that correlates with the presence or risk of late onset diabetes.

In one embodiment, the invention provides a method of detecting the genetic mutations which cause a predisposition to late onset diabetes or the disease itself, by determining the sequence of mitochondrial ATP synthase genes and/or tRNA lysine gene from subjects known to have late onset diabetes, comparing the sequence to that of known wild-type mitochondrial ATP synthase genes and/or tRNA lysine gene, and identifying mutations in the tissues of diabetic or IGT patients.

Another embodiment of the present invention involves isolated nucleic acid sequences and mutations thereof which correlate with the risk or presence of late onset diabetes. Mitochondrial DNA from both normal individuals and known late onset diabetes mellitus patients has been isolated, cloned and sequenced. In late onset diabetes patients, a small number of heteroplasmic mutations at common sites were noted.

Point mutations in mitochondrial DNA encoding ATP synthase and tRNA lysine genes were found to segregate with late-onset diabetes. In both the mitochondrial ATP synthase genes and tRNA lysine gene, the mutations occurred in one or more of clones from each individual. Detection of these and other mutations, therefore, is both predictive and diagnostic of late onset diabetes.

It is also an object of the present invention to provide cell lines whose genomic DNA is derived from cells that maintain a normal pancreatic β cell or insulin-responsive phenotype (such as, but not limited to, β TC6-F7, HIT, RINm5f, SH-SY5Y and TC-1 cells) and mitochondrial DNA having its origin in a human tissue sample derived from an individual with a disorder known to be associated with a mitochondrial defect that segregates with late onset diabetes mellitus. It is further an object of the present invention to provide an immortal $\rho°$ cell line that is undifferentiated, but is capable of being induced to differentiate, comprising cultured immortal cells having genomic DNA with origins in immortalized β cells or insulin-responsive cells (for example, TC6-F7, HIT-T15, RINm5f, TC-1, and INS-1 cells), and mitochondrial DNA having its origin in a human tissue sample derived from an individual with a disorder known to be associated with a mitochondrial defect that segregates with late onset diabetes mellitus.

Some embodiments of the present invention offer outstanding opportunities to identify, probe and characterize defective mitochondrial genes and mutations thereof that are associated with diabetes mellitus, to determine their cellular and metabolic phenotypes, and to assess the effects of various drugs and treatment regimens. In one embodiment, mitochondria from cells of a diabetes mellitus patient are transferred to immortalized β cells or insulin-responsive cells. The cells undergo phenotypic changes characteristic of late onset diabetes mellitus; for example, reduced activity of ATP synthase activity and hexokinase activity or increased production of free oxygen radicals. If exogenous agents or treatments are used on such samples and are able to prevent, delay, or attenuate the phenotypic change, then those agents or treatments warrant further study for their ability to prevent, delay or attenuate late onset diabetes mellitus in humans.

Because such cell systems are observed to undergo phenotypic changes characteristic of the diseases to which they relate, they also are used as methods of diagnosis. For example, cells are taken from an individual presenting with symptoms of late onset diabetes mellitus, and the mitochondria from those cells are put into immortalized β cells or insulin-responsive cells. Samples of these cultures are then chemically induced to differentiate into cells with pancreatic "beta cell-like" properties (e.g., insulin secretion) or insulin responsivities. If the differentiated cells that contain the patient's mitochondria begin to exhibit the degenerative phenotype that is characteristic of late onset diabetes mellitus (e.g., decreased insulin secretion), this confirms that the mitochondria carry one or more causative mtDNA mutation. It thus confirms the diagnosis of late onset diabetes mellitus.

It is another object of the invention to provide model systems for the screening of drugs effective in treating disorders associated with mitochondrial defects that segregate with late onset diabetes mellitus.

A further object of the present invention is to provide model systems for the evaluation of therapies for effectiveness in treating disorders associated with mitochondrial defects that segregate with late onset diabetes mellitus.

The invention also pertains to suppression of the undesired biological activity of the mutations, as a therapeutic treatment for late onset diabetes. More specifically, one embodiment of the invention pertains to methods of inhibiting the transcription or translation of mutant mitochondrial genes by contacting the genes with antisense sequences which are specific for mutant sequences and which hybridize to a target gene or messenger RNA transcribed therefrom. Still more specifically, the invention pertains to methods of inhibiting the transcription or translation of mutant ATP synthase genes, for example, by targeting mutant genes with antisense sequences which are specific for mutant sequences in ATP synthase or tRNA lysine genes.

An embodiment of the invention concerns the selective introduction of a conjugate molecule into mitochondria with defective ATP synthase or tRNA lysine genes. The conjugate comprises a targeting molecule conjugated to a toxin, an imaging ligand or a chemical compound having therapeutic utility, using chemical linkers. The targeting molecule can be, for example, a lipophilic cation such as an acridine orange derivative, a rhodamine 123 derivative, or a JC-1 (5,5',6,6'-tetrachloro-1,1',3,3'-tetraethylbenzimidiazolo-carbocyanine iodide) derivative. The linker can include, for example, an ester, ether, thioether, phosphorodiester, thiophosphorodiester, carbonate, carbamate, hydrazone, oxime, amino or amide functionality. The imaging ligand can be, for example, a radioisotope, hapten, biotin, enzyme, fluorophore or chemilumiphore. The toxin can be, for example, phosphate, thiophosphate, dinitrophenol, maleimide and antisense oligonucleic acids. The chemical compound having therapeutic utility may be an anti-oxidant or other useful molecule.

The present invention also comprises the transplantation of mitochondria into undifferentiated germ cells or embryonic cells, to yield organisms having mitochondria that have been wholly or partially derived from cells of a diseased organism.

These and further objects of the invention will become more apparent by the more detailed description of the invention provided herein below.

DETAILED DESCRIPTION OF THE INVENTION

Figure 1:
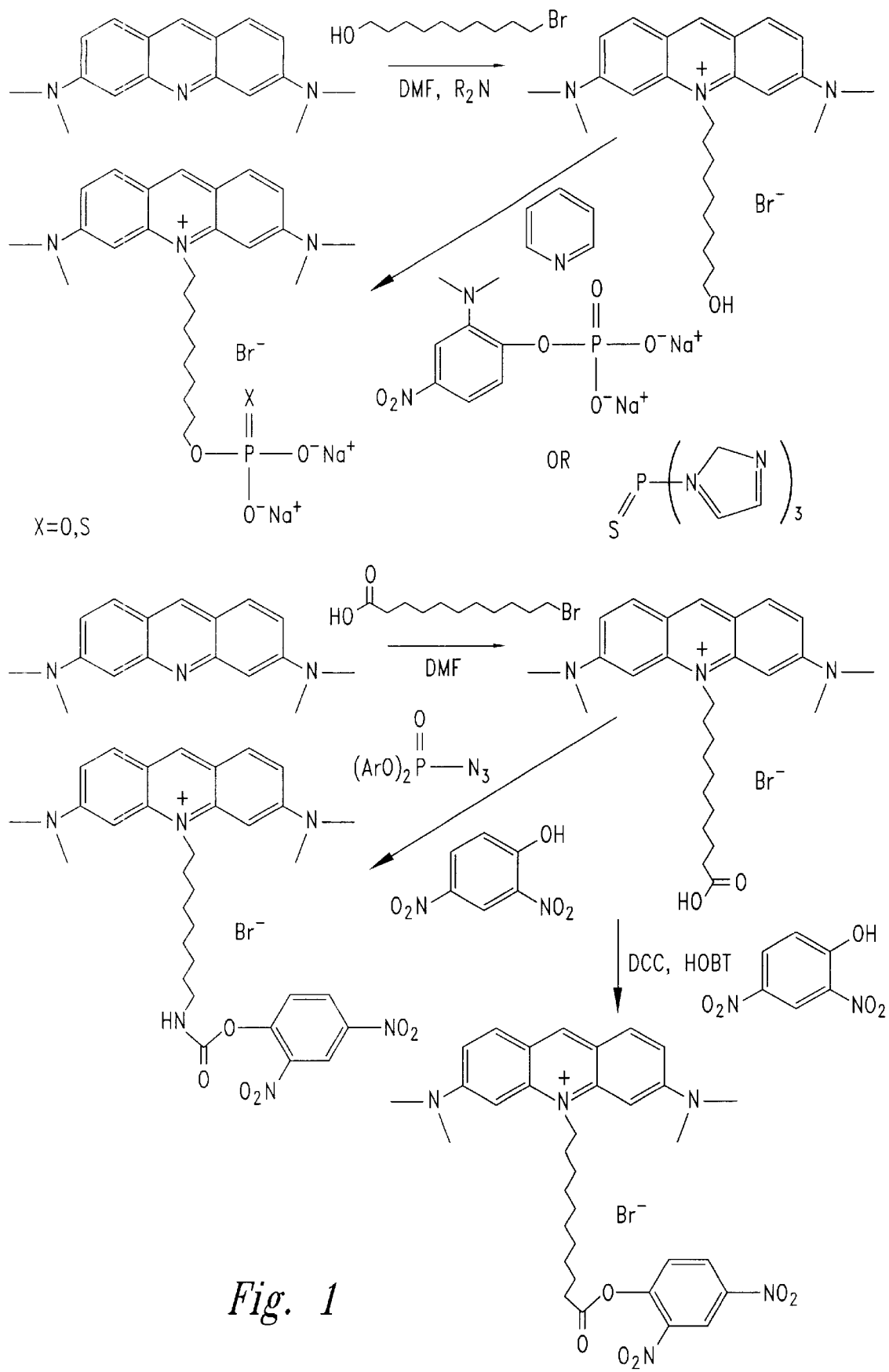
FIG. 1 illustrates a reaction scheme for the preparation of several acridine orange derivatives useful for the targeting, detection and selective destruction of defective mitochondria.

The ability to ascertain which individuals are predisposed to develop IGT and diabetes mellitus is of enormous medical significance. The elucidation of the molecular events that underlie the progression from IGT to NIDDM is a quantum leap in the understanding of these conditions. A method for delaying, minimizing or preventing the onset of IGT or diabetes mellitus represents a major therapeutic advance.

The present invention represents the first effective diagnostic assay of mitochondrial defects associated with late onset diabetes which is reliable at or before the earliest manifestations of late onset diabetes symptoms. Moreover, the invention also pertains to the suppression of the undesired biological activity of the mutations and thus affords a therapeutic treatment for late onset diabetes.

Genetic defects in the mitochondrial genes that encode components of the electron transport chain are implicated in the switch from IGT to NIDDM. Perturbations of this protein complex predictably lead to an alteration in the production of adenosine triphosphate (ATP), the main source of energy for cellular biochemical reactions.

When mitochondrial intracellular ATP levels drop, glucose transport into cells is impaired, metabolism of glucose is slowed and insulin secretion is decreased, all critical events in the switch from IGT to diabetes mellitus. Affected tissues are striated muscle (the major insulin-sensitive tissue) and pancreatic beta cells (insulin secreting cells). These target tissues contain non-dividing terminally differentiated cells that are susceptible to accumulation of mtDNA mutations. Achieving a threshold level of mutations in mtDNA in pancreatic beta cells could precipitate a drop in insulin secretion, providing a molecular mechanism for the switch in disease phenotype from IGT to diabetes mellitus. In addition, a similar mechanism may precipitate a loss of insulin responsivity in muscle.

Certain critical enzymes in the metabolism of glucose (hexokinases) and insulin secretion require ATP for proper function. Hexokinases and in particular glucokinase are bound to porin, a voltage dependent anion channel, located within the outer mitochondrial membrane. Porin, in turn, is apposed to the adenine nucleotide translocator of the inner mitochondrial membrane. Together these protein complexes form a conduit for delivery of ATP from the inner mitochondrial matrix to hexokinases bound to the outer membrane and for return of ADP generated by catalytic activity of these kinases. The ATP used by mitochondrial bound hexokinases is derived primarily from the mitochondrial matrix and not the cytoplasm. Hexokinases require mitochondrial ATP for activation.

ATP synthase is an important component of the cellular energy generating system and is located in the mitochondria of eukaryotic cells. ATP synthase, also known as complex V, is composed of at least eight subunits. At least six of these subunits are encoded by nuclear genes; the remaining two subunits (6 and 8) are encoded by mitochondrial genes.

Without wishing to be held to any particular theory, it has been postulated that the destructive effects of mutations in the ATP synthase gene arise from the production of oxygen radicals and other chemically unstable molecules due to collapse of the proton gradient across the intramitochondrial membrane. The effects of such free radicals is expected to be cumulative, especially in view of the lack of mechanisms for suppressing mutations in mitochondria.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise.

The terms used herein are not intended to be limiting of the invention. For example, the term "gene" includes cDNAs, RNA, or other polynucleotides that encode gene products. In using the terms "nucleic acid", "RNA", "DNA", etc., we do not mean to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives can be made and will hybridize to one another and to DNA and RNA, and the use of such analogues and derivatives is also within the scope of the present invention. "Expression" of a gene or nucleic acid encompasses not only cellular gene expression, but also the transcription and translation of nucleic acid(s) in cloning systems and in any other context. "At least one mutation" denotes the substitution, addition or deletion of at least one nucleotide anywhere in the mitochondrial genome that is not present in a wild-type mitochondrial genome, whose phenotype correlates with diabetes mellitus. "Point mutations" are mutations within a nucleotide sequence that result in a change from one nucleotide to another; "silent mutations" are mutations that do not result in a change in the amino acid sequence encoded by the nucleotide sequence.

The term "tissue" includes blood and/or cells isolated or suspended from solid body mass, as well as the solid body mass of the various organs. "Immortal" cell lines denotes cell lines that are so denoted by persons of ordinary skill, or are capable of being passaged preferably an indefinite number of times, but not less than ten times, without significant phenotypical alteration. "$\rho^\circ$ cells" are cells essentially depleted of functional mitochondria and/or mitochondrial DNA, by any method useful for this purpose.

The term "diabetes mellitus" is used in the claims to denote the disease that exhibits the symptoms of diabetes mellitus recognizable to one of ordinary skill in the art. A phenotypic trait, symptom, mutation or condition "correlates" with diabetes mellitus if it is repeatedly observed in individuals diagnosed as having some form of diabetes mellitus, or if it is routinely used by persons of ordinary skill in the art as a diagnostic criterion in determining that an individual has diabetes mellitus or a related condition. Examples include: impaired insulin secretion, impaired response to insulin, or both.

Pre-clinical and/or asymptomatic conditions that correlate with the presence of mitochondrial mutations often observed in patients with diabetes mellitus, such as IGT, may represent steps in the progression in the disease. Individuals that lack the full panoply of such symptoms but carry mutations that "correlate" with diabetes mellitus are hereby defined as being "at risk" or having a "predisposition" for developing the fully symptomatic disease.

Although the invention focuses preferentially on humans afflicted with or at risk for developing diabetes mellitus as defined above, the invention also encompasses the analysis of tissues and preparations from relatives of persons having or "at risk" for developing diabetes mellitus (which relatives may or may not themselves be at risk), and in vivo and in vitro animal and tissue culture models that may exhibit one or more or all of the symptoms that correlate with the mitochondrial mutations of the invention.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

Although the cells suggested for certain embodiments herein are immortalized pancreatic β cells, adipocytes, neuronal tissue, myoblasts and insulin-responsive cells and platelets, the present invention is not limited to the use of such cells. Cells from different tissues (breast epithelium, colon, lymphocytes, etc.) or different species (human, mouse, etc.) are also useful in the present invention.

Throughout this application various publications are referenced within parentheses. The disclosures of these publications in their entireties are hereby incorporated by reference in this application in order to more fully describe the state of the art to which the present invention pertains.

Diagnostic Detection of Late Onset Diabetes-Associated Mutations Using Hybridization and Ligation Techniques In one embodiment of the present invention, base changes in the mitochondrial ATP synthase and tRNA lysine genes are detected and used as a diagnostic for late onset diabetes.

A variety of techniques are available for isolating DNA and RNA from patient blood samples and for detecting mutations in isolated mitochondrial ATP synthase and tRNA lysine genes. For example, the DNA from a blood sample is obtained by cell lysis following alkali treatment. Often, there are multiple copies of RNA message per DNA. Accordingly, it is useful from the standpoint of detection sensitivity to have a sample preparation protocol which isolates both forms of nucleic acid. Total nucleic acid may be isolated by guanidium isothiocyanate/phenol-chloroform extraction, or by proteinase K/phenol-chloroform treatment. Commercially available sample preparation methods such as those from Qiagen Inc. (Chatsworth, Calif.) are also utilized.

As discussed more fully hereinbelow, hybridization with one or more of labelled probes containing the variant sequences under stringency conditions that result in specific binding to sequences complementary to these probes enables detection of the late onset diabetes mutations. Since each late onset diabetes patient can be heteroplasmic (possessing both the late onset diabetes mutations and the normal sequence), a quantitative or semi-quantitative measure (depending on the detection method) of such heteroplasmy is obtained by comparing the amount of signal from the late onset diabetes probe to the amount from the late onset diabetes (normal) probe.

Certain techniques, discussed more fully hereinbelow, are available for detecting the specific mutations in the mitochondrial ATP synthase and tRNA lysine genes. The detection methods include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Cloning and sequencing of the ATP synthase and/or tRNA lysine genes serves to detect late onset diabetes mutations in patients. Sequencing is carried out with commercially available automated sequencers utilizing labelled primers or terminators. An alternate sequencing strategy is the sequencing by hybridization method using high density oligonucleotide arrays on silicon chips (Fodor et al., *Nature* 364: 555–556 (1993); Pease et al., *Proc. Nat. Acad. Sci. USA* 91: 5022–5026 (1994)). Labelled target nucleic acid generated, for example, from PCR amplification of the target genes using fluorescently labelled primers, is hybridized with a chip containing a set of short oligonucleotides which probe regions of complementarity with the target sequence. The resulting hybridization patterns are used to reassemble the original target DNA sequence.

Mutational analysis is also carried out by methods based on ligation of oligonucleotide sequences which anneal immediately adjacent to each other on a target DNA or RNA molecule (Wu and Wallace, *Genomics* 4: 560–569 (1989); Landren et al., *Science* 241: 1077–1080 (1988); Nickerson et al., *Proc. Natl. Acad. Sci.* 87: 8923–8927 (1990); Barany, F., *Proc. Natl. Acad. Sci.* 88: 189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permits the ligation reaction to be conducted with high stringency (Barany, F., *PCR Methods and Applications* 1: 5–16 (1991)).

Analysis of point mutations in DNA is also carried out by using the polymerase chain reaction (PCR) and variations thereof (e.g., using 7-deaza GTP with or instead of dGTP). Mismatches are detected by competitive oligonucleotide priming under hybridization conditions where binding of the perfectly matched primer is favored (Gibbs et al., *Nucl. Acids. Res.* 17: 2437–2448 (1989)). In the amplification refractory mutation system technique (ARMS), primers are designed to have perfect matches or mismatches with target sequences either internal or at the 3' residue (Newton et al., *Nucl. Acids. Res.* 17: 2503–2516 (1989)). Under appropriate conditions, only the perfectly annealed oligonucleotide functions as a primer for the PCR reaction, thus providing a method of discrimination between normal and mutant (late onset diabetes) sequences.

Genotyping analysis of the ATP synthase and tRNA lysine genes is also carried out using single nucleotide primer-guided extension assays, where the specific incorporation of the correct base is provided by the high fidelity of the DNA polymerase (Syvanen et al., *Genomics* 8: 684–692 (1990); Kuppuswamy et al., *Proc. Natl. Acad. Sci. U.S.A.* 88: 1143–1147 (1991)). Another primer extension assay which allows for the quantification of heteroplasmy by simultaneously interrogating both wild-type and mutant nucleotides, is disclosed in a co-pending U.S. application entitled "Multiplexed Primer Extension Methods", naming Eoin Fahy and Soumitra Ghosh as inventors, filed in March 1995, serial number to be assigned, the disclosure of which is incorporated by reference.

Detection of single base mutations in target nucleic acids is conveniently accomplished by differential hybridization techniques using target-specific oligonucleotides (Suggs et al., *Proc. Natl. Acad. Sci.* 78: 6613–6617 (1981); Conner et al., *Proc. Natl. Acad. Sci.* 80: 278–282 (1983); Saiki et al., *Proc. Natl. Acad. Sci.* 86: 6230–6234 (1989)). Mutations are diagnosed on the basis of the higher thermal stability of the perfectly matched probes as compared to the mismatched probes. The hybridization reactions are carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

An alternative strategy involves detection of the ATP synthase and/or tRNA lysine genes by sandwich hybridization methods. In this strategy, the mutant and wildtype (normal) target nucleic acids are separated from non-homologous DNA/RNA using a common capture oligonucleotide immobilized on a solid support and detected by specific oligonucleotide probes tagged with reporter labels. The captured oligonucleotides are immobilized on microtitre plate wells or on beads (Gingeras et al., *J. Infect. Dis.* 164: 1066–1074 (1991); Richman et al., *Proc. Natl. Acad. Sci.* 88: 11241–11245 (1991)).

While radio-isotopic labeled detection oligonucleotide probes are highly sensitive, non-isotopic labels are preferred due to concerns about handling and disposal of radioactivity. A number of strategies are available for detecting target nucleic acids by non-isotopic means (Matthews et al., *Anal. Biochem.*, 169: 1–25 (1988)). The non-isotopic detection method are either direct or indirect.

The indirect detection process is generally where the oligonucleotide probe is covalently labelled with a hapten or ligand such as digoxigenin (DIG) or biotin. Following the hybridization step, the target-probe duplex is detected by an antibody- or streptavidin-enzyme complex. Enzymes commonly used in DNA diagnostics are horseradish peroxidase and alkaline phosphatase. One particular indirect method, the Genius detection system (Boehringer Mannheim) is especially useful for mutational analysis of mitochondrial genes. This indirect method uses digoxigenin as the tag for the oligonucleotide probe and is detected by an anti-digoxigenin-antibody-alkaline phosphatase conjugate.

Direct detection methods include the use of fluorophor-labeled oligonucleotides, lanthanide chelate-labeled oligonucleotides or oligonucleotide-enzyme conjugates. Examples of fluorophor labels are fluorescein, rhodamine and phthalocyanine dyes. Examples of lanthanide chelates include complexes of $Eu^{3+}$ and $Tb^{3+}$. Directly labeled oligonucleotide-enzyme conjugates are preferred for detecting point mutations when using target-specific oligonucleotides as they provide very high sensitivities of detection.

Oligonucleotide-enzyme conjugates are prepared by a number of methods (Jablonski et al., *Nucl. Acids Res.*, 14: 6115–6128 (1986); Li et al., *Nucl. Acids Res.* 15: 5275–5287 (1987); Ghosh et al., *Bioconiugate Chem.* 1: 71–76 (1990)), and alkaline phosphatase is the enzyme of choice for obtaining high sensitivities of detection. The detection of target nucleic acids using these conjugates is carried out by filter hybridization methods or by bead-based sandwich hybridization (Ishii et al., *Bioconiugate Chemistry* 4: 34–41 (1993)).

Detection of the probe label is accomplished by the following approaches. For radioisotopes, detection is by autoradiography, scintillation counting or phosphor imaging. For hapten or biotin labels, detection is with antibody or streptavidin bound to a reporter enzyme such as horseradish peroxidase or alkaline phosphatase, which is then detected by enzymatic means. For fluorophor or lanthanide-chelate labels, fluorescent signals are measured with spectrofluorimeters with or without time-resolved mode or using automated microtitre plate readers. With enzyme labels, detection is by color or dye deposition (p-nitrophenyl phosphate or 5-bromo-4-chloro-3-indolyl phosphate/nitroblue tetrazolium for alkaline phosphatase and 3,3'-diaminobenzidine-$NiCl_2$ for horseradish peroxidase), fluorescence (e.g., 4-methyl umbelliferyl phosphate for alkaline phosphatase) or chemiluminescence (the alkaline phosphatase dioxetane substrates LumiPhos 530 from Lumigen Inc., Detroit, Mich. or AMPPD and CSPD from Tropix, Inc.). Chemiluminescent detection is carried out with X-ray or polaroid film or by using single photon counting luminometers. This is the preferred detection format for alkaline phosphatase labelled probes.

The detection oligonucleotide probes range in size between 10–100 bases, and are preferably between 15 to 30 bases in length. In order to obtain the required target discrimination using the detection oligonucleotide probes, the hybridization reactions are generally run between 20°–60° C., and most preferably between 30°–50° C. As known to those skilled in the art, optimal discrimination between perfect and mismatched duplexes is obtained by manipulating the temperature and/or salt concentrations or inclusion of formamide in the stringency washes.

Diagnostic Detection of Diabetes Associated Mutations Using Antibodies

As an alternative to detection of mutations in the nucleic acids associated with the mutant mitochondrial genes described herein, the protein products of these genes are analyzed using immune techniques. In particular, altered proteins (variant polypeptides) encoded by nucleic acids having point mutations in ATP synthase subunit 8 are isolated and used to prepare antisera and monoclonal antibodies that specifically detect the products of the mutated genes and not those of non-mutated or wild-type genes. Mutated gene products also are used to immunize animals for the production of polyclonal antibodies. Recombinantly produced peptides can also be used to generate polyclonal antibodies. These peptides represent small fragments of gene products produced by expressing regions of the mitochondrial genome containing point mutations.

As discussed, for example, in PCT/US93/10072, variant polypeptides encoded by nucleic acids with point mutations in ATP synthase subunit 8 are used to immunize an animal for the production of polyclonal antiserum. For example, a recombinantly produced fragment of a variant polypeptide is injected into a mouse along with an adjuvant so as to generate an immune response. Murine immunoglobulins which bind the recombinant fragment with a binding affinity of at least $1 \times 10^7$ $M^{-1}$ are harvested from the immunized mouse as an antiserum, and are optionally further purified by affinity chromatography or other means. Additionally, spleen cells are harvested from the mouse and fused to myeloma cells to produce a bank of antibody-secreting hybridoma cells. The bank of hybridomas is screened for clones that secrete immunoglobulins which bind the recombinantly produced fragment with an affinity of at least $1 \times 10^6$ $M^{-1}$. More specifically, immunoglobulins that selectively bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Nucleic acid sequences capable of ultimately expressing the desired variant polypeptides are formed from a variety of different polynucleotides (genomic or cDNA, RNA, synthetic oligonucleotides, etc.) as well as by a variety of different techniques.

The DNA sequences are expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362, incorporated herein by reference thereto.

Polynucleotides encoding a variant polypeptide include sequences that facilitate transcription (expression sequences) and translation of the coding sequences such that the encoded polypeptide product is produced. Construction of such polynucleotides is well known in the art. For example, such polynucleotides include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

*E. coli* is one prokaryotic host useful particularly for cloning DNA sequences of the present invention. Other microbial hosts suitable for use include bacilli, such as *Bacillus subtilus*, and other enterobacteriaceae, such as Salmonella, Serratia, and various Pseudomonas species. Expression vectors are made in these prokaryotic hosts which will typically contain expression control sequences compatible with the host cell (e.g., an origin of replication). In addition, any number of a variety of well-known promoters are used, such as the lactose promoter system, a tryptophan (Trp) promoter system, a beta-lactamase promoter system, or a promoter system from phage lambda. The promoters typically control expression, optionally with an operator sequence, and have ribosome binding site sequences, for example, for initiating and completing transcription and translation.

Other microbes, such as yeast, are used for expression. Saccharomyces is a suitable host, with suitable vectors having expression control sequences, such as promoters, including 3-phosphoglycerate kinase or other glycolytic enzymes, and an origin of replication, termination sequences, etc. as desired.

In addition to microorganisms, mammalian tissue cell culture is used to express and produce the polypeptides of the present invention. Eukaryotic cells are preferred, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, and so forth. The vectors containing the DNA segments of interest (e.g., polypeptides encoding a variant polypeptide) are transferred into the host cell by well-known methods, which vary depending on the type of cellular host. For example, calcium chloride transfection is commonly utilized for prokaryotic cells, whereas calcium phosphate treatment or electroporation is useful for other cellular hosts.

Test Kits

The method lends itself readily to the formulation of test kits for use in diagnosis. Such a kit comprises a carrier compartmentalized to receive in close confinement one or more containers wherein a first container contains suitably labeled DNA or immulogical probes. Other containers contain reagents useful in the localization of the labeled probes, such as enzyme substrates. Still other containers contain restriction enzymes, buffers etc., together with instructions for use.

Antisense Embodiments

Protein synthesis may be inhibited the use of antisense or triplex oligonucleotides, analogues or expression constructs. These methods entail introducing into a cell a nucleic acid sufficiently complementary in sequence so as to specifically hybridize to a target nucleic acid. Antisense methodology inhibits the normal processing, translation or half-life of the target nucleic acid. A variety of antisense methods are well known to one skilled in the art. Hélenè et al., *Biochem. Biophys. Acta* 1049: 99–125 (1990). Procedures for inhibiting gene expression in cell culture and in vivo can be found, for example, in C. F. Bennett, et al. *J. Liposome Res.*, 3: 85 (1993) and C. Wahlestedt, et al. *Nature,* 363: 260 (1993).

Suppressing the effects of the mutations through antisense technology provides an effective therapy for diabetes mellitus. Antisense agents target mitochondrial DNA, by triplex formation with double-stranded DNA, by duplex formation with single stranded DNA during transcription, or both. Antisense agents also target messenger RNA coding for the mutated cytochrome oxidase gene(s). Since the sequences of both the DNA and the mRNA are essentially the same, it is not necessary to determine accurately the precise target to account for the desired effect.

As used herein, an "antisense" oligonucleotide is one that base pairs with single stranded DNA or RNA by Watson-Crick base pairing and with duplex target DNA via Hoogsteen hydrogen bonds. Antisense and triplex methods generally involve the treatment of cells or tissues with a relatively short oligonucleotide, although longer sequences are used to achieve inhibition. The oligonucleotide is either deoxyribo- or ribonucleic acid or analogues thereof, and must be of sufficient length to form a stable duplex or triplex with the target RNA or DNA at physiological temperatures and salt concentrations. It should also be of sufficient complementarity or sequence specificity to specifically hybridize to the target nucleic acid. Oligonucleotide lengths sufficient to achieve this specificity are generally about 10 to 60 nucleotides long, preferably about 10 to 20 nucleotides long. However, hybridization specificity is not only influenced by length and physiological conditions but may also be influenced by such factors as GC content and the primary sequence of the oligonucleotide. Such principles are well known in the art.

The composition of the antisense or triplex oligonucleotides influences the efficiency of inhibition. For example, it is preferable to use oligonucleotides that are resistant to degradation by the action of endogenous nucleases. Nuclease resistance will confer a longer in vivo half-life to the oligonucleotide thus increasing its efficacy and reducing the required dose.

Antisense therapy is extremely efficient since only a few copies per cell are required to achieve complete inhibition. Greater efficacy is obtained by modifying the oligonucleotide so that it is more permeable to cell membranes. Such modifications are well known in the art and include the alteration of the negatively charged phosphate backbone bases, or modification of the sequences at the 5' or 3' terminus with agents such as intercalators and cross-linking molecules. Specific examples of such modifications include oligonucleotide analogs that contain methylphosphonate (Miller, P. S., *Biotechnology* 2: 358–362 (1991)), phosphorothioate (Stein, *Science* 261: 1004–1011 (1993)) and phosphorodithioate linkages (Brill, W. K-D., *J. Am. Chem. Soc.* 111: 2322 (1989)). Other types of linkages and modifications exist as well, such as a polyamide backbone in peptide nucleic acids (Nielson et al., *Science* 254: 1497 (1991)), formacetal (Matteucci, M., *Tetrahedron Lett.* 31: 2385–2388 (1990)) carbamate and morpholine linkages as well as others known to those skilled in the art.

Vectors containing antisense nucleic acids are employed to express antisense message to reduce the expression of the target nucleic acid and therefore its activity. Such vectors are known or can be constructed by those skilled in the art and should contain all expression elements necessary to achieve the desired transcription of the antisense or triplex sequences. Other beneficial characteristics are also contained within the vectors such as mechanisms for recovery of the nucleic acids in a different form.

Phagemids are a specific example of such beneficial vectors because they are used either as plasmids or as bacteriophage vectors. Examples of other vectors include viruses, such as bacteriophages, baculoviruses and retroviruses, cosmids, plasmids, liposomes and other recombination vectors. The vectors also contain elements for use in either procaryotic or eukaryotic host systems. One of ordinary skill in the art will known which host systems are compatible with a particular vector.

The vectors are introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by references, and in Ausubel et al., Current Protocols in Molecular Biology, John Wiley and Sons, Baltimore, Md. (1989), which is also hereby incorporated by reference. The methods include, for example, stable or transient transfection, lipofection, electroporation and infection with recombinant viral vectors.

Introduction of nucleic acids by infection offers several advantages over the other listed methods which includes their use in vitro and in vivo. Higher efficiency is achieved due to their infectious nature. Moreover, viruses are very specialized and typically infect and propagate in specific cell types. Thus, their natural specificity is used to target the antisense vectors to specific cell types in vivo or within a tissue or mixed culture of cells. Viral vectors are also modified with specific receptors or ligands to alter target specificity through receptor mediated events.

A specific example of a viral vector for introducing and expressing antisense nucleic acids is the adenovirus derived vector Adenop53TX. This vector expresses a herpes virus thymidine kinase (TX) gene for either positive or negative selection and an expression cassette for desired recombinant sequences such as antisense sequences. This vector is used to infect cells including most cancers of epithelial origin, glial cells and other cell types. This vector, as well as others that exhibit similar desired functions, is used to treat a mixed population of cells to selectively express the antisense sequence of interest. A mixed population of cells can include, for example, in vitro or ex vivo culture of cells, a tissue or a human subject.

Additional features can be added to the vector to ensure its safety and/or enhance its therapeutic efficacy. Such features include, for example, markers that are used to negatively select against cells infected with the recombinant virus. An example of such a negative selection marker is the TK gene described above that confers sensitivity to the antibiotic gancyclovir. Negative selection is therefor a means by which infection is controlled because it provides inducible suicide through the addition of antibiotics. Such protection ensures that if, for example, mutations arise that produce mutant forms of the viral vector or antisense sequence, cellular transformation will not occur. Moreover, features that limit expression to particular cell types can also be included. Such features include, for example, promoter and expression elements that are specific for the desired cell type.

In addition to the specificity afforded by the antisense agents, the target RNA or genes are irreversibly modified by incorporating reactive functional groups in these molecules which covalently link the target sequences, e.g., by alkylation.

In a preferred embodiment, antisense agents target messenger RNA coding for the mutated ATP synthase or tRNA lysine. Since the sequences of both the DNA and the mRNA are the same, it is not necessary to determine accurately the precise target to account for the desired effect.

To demonstrate the ability to affect expression of mitochondrial ATP synthase or tRNA lysine genes, an oligonucleotide designed to hybridize near the 5'-end of the wild type ATP synthase or tRNA lysine gene or gene transcript is synthesized. When the antisense oligonucleotide is present in a suitable cell culture, the cells will die if the electron transport chain is interrupted. Control fibroblasts treated with complementary ('sense') oligonucleotide, or left untreated, will exhibit no such effects.

The diagnostic test of the present invention is used to determine which of the specific late onset diabetes mutations exist in a particular late onset diabetes patient; this allows for "custom" treatment of the patient with antisense oligonucleotides directed only to the detected mutations. When combined with the present diagnostic test, this approach to "patient-specific therapy" results in treatment restricted to the specific mutations detected in a patient.

Antisense oligonucleotide therapeutic agents with a high degree of pharmaceutical specificity allow for the combination of two or more antisense therapeutics at the same time, without increased cytotoxic effects. Thus, when a patient is diagnosed as having two or more late onset diabetes mutations in ATP synthase or tRNA lysine genes, the therapy is tailored to treat the multiple mutations simultaneously. This patient-specific therapy circumvents the need for 'broad spectrum' antisense treatment using all possible mutations and minimizes the exposure of the patient to any unnecessary antisense therapeutic treatment. The end result is less costly treatment, with less chance for toxic side effects.

Depletion of Mitochondria

The present invention also provides methods for the selective destruction of target mitochondria and the accumulation of therapeutically useful agents into target mitochondria. Since the mitochondrial genome is heteroplasmic (i.e., it contains mutated and normal DNA), destruction of target mitochondria carrying mutations will leave intact mitochondria carrying normal or wild-type DNA and these normal mitochondria will repopulate the targeted tissue, normalizing mitochondrial function. Alternatively, accumulating a therapeutically useful agent into mutant or wild-type DNA carrying mitochondrial mutations will protect these mitochondria from further damage.

This selective destruction or drug targeting can be accomplished by identifying unique characteristics of mitochondria carrying mutated DNA, designing a small molecule that is directed at one or more of these unique characteristics, and conjugating a mitochondrial toxin or therapeutically useful agent to this small molecule. (A "targeting molecule" is any molecule that selectively accumulates in mitochondria having defective cytochrome oxidase activity, and includes acridine orange derivatives and JC-1 derivatives as discussed hereinbelow; "Mitochondrial toxins" are molecules that destroy or disable the selected mitochondria, and include phosphate, thiophosphate, dinitrophenolate, maleimide and antisense oligonucleotides such as those discussed above.) The toxin will be concentrated within the defective mitochondria by the targeting molecule and will disable or destroy selectively the defective mitochondria. Therapeutically useful compounds are molecules that interfere with the production of oxygen radicals or trap oxygen radicals in an inert form once they are produced, such as, for example, antioxidants and radical spin trapping agents.

The molecule may be an active mitochondrial toxin or therapeutic agent in its conjugated form. However, it is preferred to design the molecule such that it is inactive in its conjugated form.

The chemical linkage between the targeting molecule and the toxin or therapeutic agent may be a substrate for a mitochondria-specific enzyme or sensitive to redox cleavage. Choice of the linkage depends upon the chemical nature of the targeting molecule and toxin and the requirements of the cleavage process. Once the conjugate is concentrated in the defective mitochondria, the toxin or therapeutic agent is cleaved from the targeting molecule, activating the toxin or releasing the therapeutic agent.

Mitochondria with defective ATP synthase activity exhibit decreased synthesis of adenosine triphosphate and general bioenergetic failure. As a consequence, mitochondria carrying mutated DNA will become enlarged and the intramitochondrial membrane potential will increase.

Enlarged mitochondria have increased levels of cardiolipin and other negatively charged phospholipids. The acridine orange derivative 10N-nonylacridine orange (NAO) binds relatively specifically to cardiolipin and accumulates in dysfunctional mitochondria. The accumulation of NAO and other chemical derivatives of acridine orange, including but not limited to those with aliphatic chains of variable length attached to the ring nitrogen of acridine orange ([3,6-bis (dimethyl-amino) acridine]), such as 10N-pentylacridine orange, 10N-octylacridine orange, and dodecylacridine orange, is independent of the mitochondrial transmembrane potential. Maftah et al., *Biochemical and Biophysical Research Communications* 164(1): 185–190 (1989)). At concentrations up to 1 $\mu$M, NAO and its derivatives can be used to target other molecules to the inner mitochondrial matrix. If the NAO is chemically linked to a mitochondrial toxin such as phosphate, thiophosphate, dinitrophenolate, maleimide and antisense oligonucleotides, or to a therapeutically useful molecule such as an antioxidant, radical spin trapping agent, etc., then mitochondria accumulating the NAO-mitochondrial toxin conjugate or therapeutic conjugate can be selectively disabled, destroyed or protected. Alternately, at high concentrations (3–10 $\mu$M) NAO and its derivatives inhibit electron transport, ATP hydrolysis and $P_i$-transport and disrupt respiration. (Maftah et al., *FEBS Letters* 260(2): 236–240 (1990). At these concentrations, NAO is mitochondrial toxin.

According to an embodiment of the present invention, the terminus of any aliphatic or other type of chain (such as polyethylene glycol) attached to the ring nitrogen of acridine orange is chemically derivatized with carboxylic acid, hydroxyl, sulfhydryl, amino or similar groups to accept any mitochondrial toxin. In other embodiments, additional sites of attachment of the mitochondrial toxin to acridine orange and acridine orange derivatives are selected. For example, the 10-N-(10-hydroxy-1-decyl)-3,6-bis(dimethylamino) acridine bromide salt may be prepared and further derivatized to 10-N-(10-phosphoryl-1-decyl)-3,6-bis (dimethylamino) acridine chloride salt or 10-N-(10-thiophosphoryl-1-decyl)-3,6-bis(dimethylamino)acridine chloride salt. Alternately, 10-N-(11-undecanoic acid)-3,6-bis (dimethylamino)acridine bromide salt may be prepared and further derivatized to 10-N-(11-undecan-1-oic acid 2,4-dinitrophenolate)-3,6-bis(dimethylamino) acridine bromide salt.

Upon cleavage, the phosphate, thiphospate or dinitrophenol levels selectively increase within defective mitochondria and destroy them. The functionalization and covalent attachment of the toxin does not need to depend on subsequent release of the toxin by cleavage of the NAO from the toxin, if the attachment point on the toxin is non-interfering with the function of the toxin within the mitochondria.

Several examples of the preparation of acridine orange derivatives are summarized in FIG. 1 and in Examples IX(a)–IX(f) hereinbelow. Other modifications are permitted as known to those skilled in the art.

Still other embodiments of the present invention target changes in the intramitochondrial membrane potential due to defective ATP synthase activity. Delocalized lipophilic cations have been used to monitor mitochondrial membrane potential. The uptake of these cations is related to the presence of the negative sink inside the mitochondria created by the proton pump. As mitochondria increase in size due to ATP synthase or tRNA lysine defects, the transmembrane potential will increase and these defective mitochondria will accumulate lipophilic cations. According to an embodiment of the present invention, these lipophilic cations are conjugated to mitochondrial toxins or therapeutically useful agents and used to destroy or protect defective mitochondria that possess increased transmembrane potentials. Rhodamine-123 has been used extensively to monitor mitochondrial membrane potential and can conjugate to mitochondrial toxins to concentrate toxins within the mitochondria. The compound 5,5',6,6'-tetrachloro-1,1',3,3'-tetraethylbenzimidiazolo-carbocyanine iodide (JC-1) also accumulates in mitochondria dependent upon the transmembrane potential. When JC-1 exceeds a critical concentration, J-aggregates form in the mitochondrial matrix, and their size causes these JC-1 J-aggregates to diffuse slowly out of the mitochondria (Reers et al., *Biochemistry*, 30(18): 4480–4486 (1991)). JC-1 may be chemically conjugated to a mitochondrial toxin or therapeutically useful agent, producing a long-lived toxic or therapeutic compound to mitochondria displaying increased transmembrane potential relative to normal mitochondria.

As with NAO, by adding a functional group to the JC-1 structure one can covalently attach another chemical entity to the JC-1 subunit. Delivery to the cells then causes the dual agent to be preferentially transported into the mitochondria, where the dual agent may be cleaved at the covalent attachment to release a toxin or therapeutically useful agent within the mitochondria where it exerts the desired effect. Alternatively, the functionalization and covalent attachment of the toxin or therapeutically useful agent does not need to depend on subsequent release of the toxin or therapeutically useful agent by cleavage of the JC-1 from the active agent, if the attachment point on the active species is non-interfering with the function of the toxin or therapeutically useful agent within the mitochondria.

Figure 2:
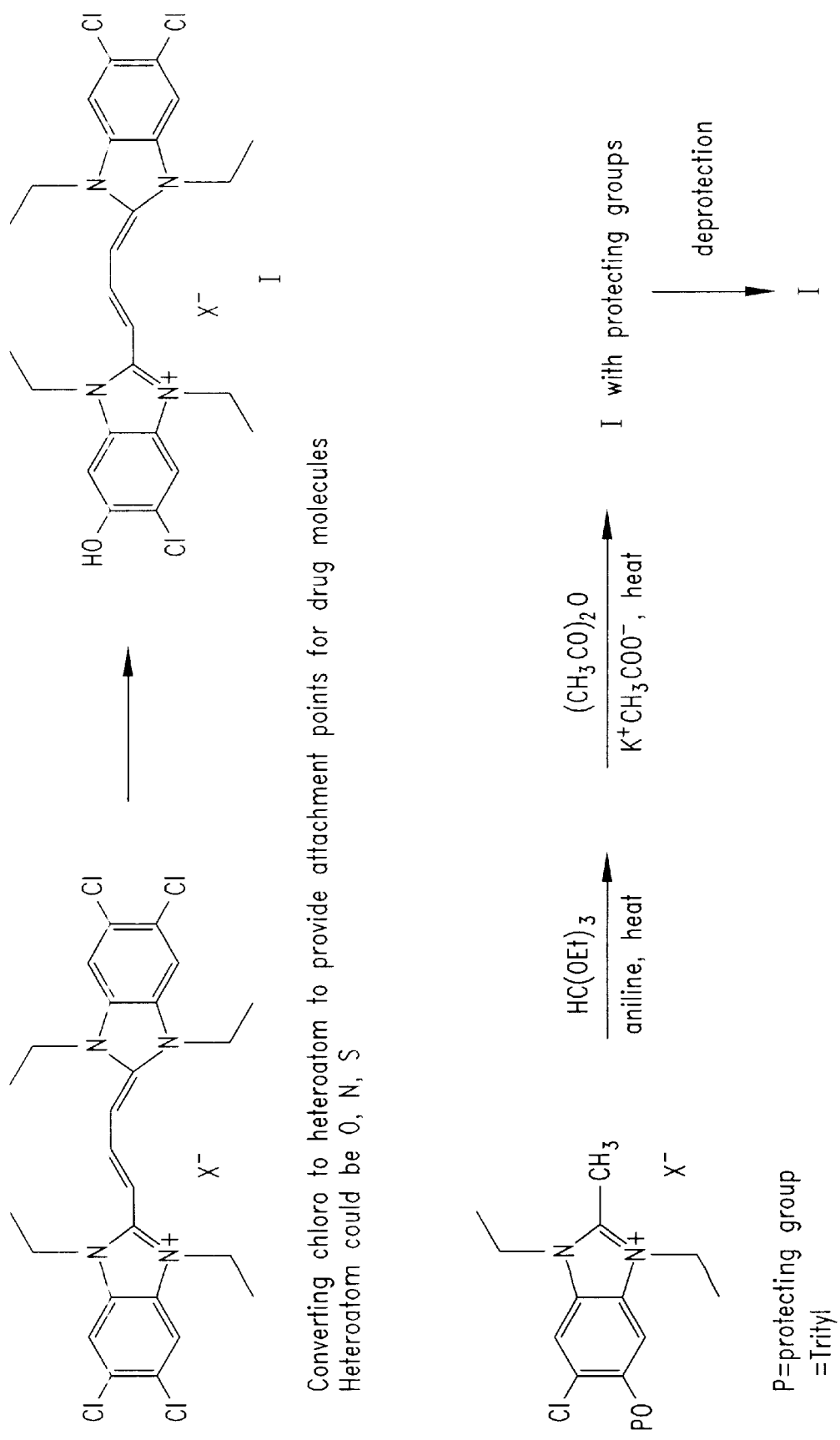
FIGS. 2–5 illustrate reaction schemes for the preparation of several JC-1 derivatives useful for the targeting, detection and selective destruction of defective mitochondria.
Figure 3:
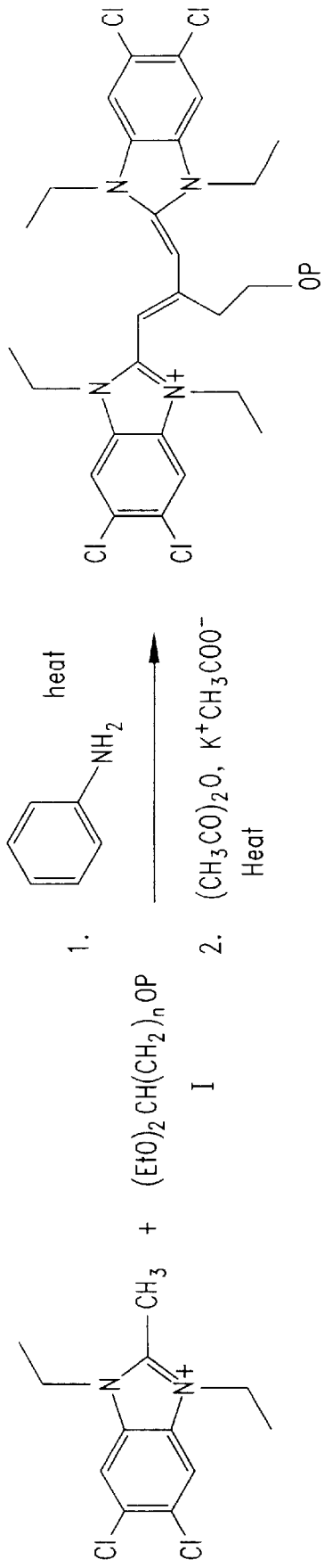
Figure 4:
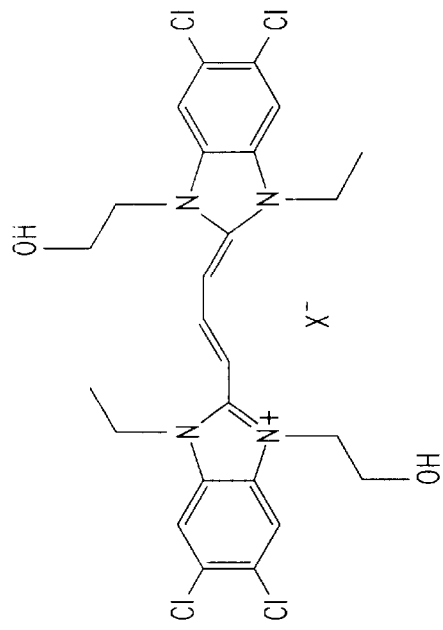
Figure 4:
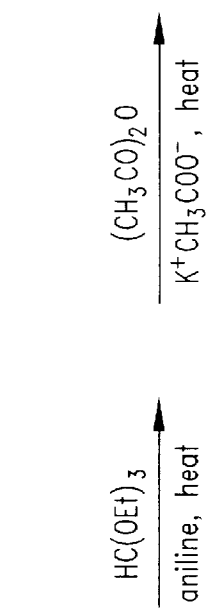
Figure 4:
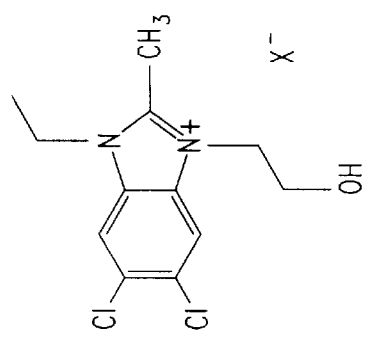
Figure 5:
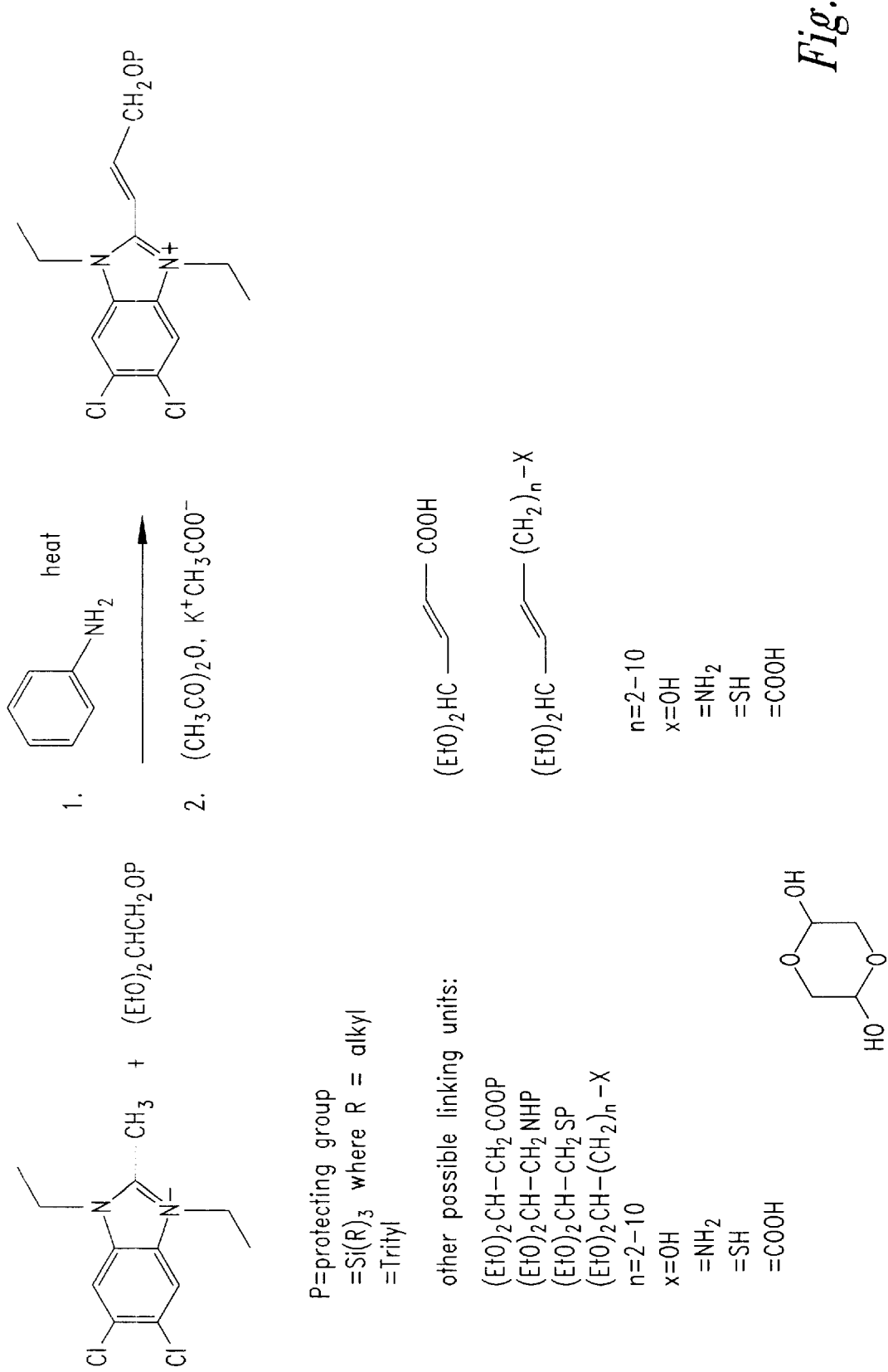

FIGS. 2, 3 and 4 outline the functionalization of JC-1 by several different methods. Examples IX(g)–IX(f) hereinbelow illustrate an oxygen functionality, but the same can be accomplished with a nitrogen, sulfur or carboxylic acid functionality.

By utilizing the quasi-symmetrical nature of JC-1, a new chemical entity may be synthesized that is "half" JC-1 and contains a functional group capable of being used as a point for covalent attachment of another chemical entity to the JC-1 subunit. The existence of the JC-1 subunit facilitates selective transport of the whole molecule to the mitochondria where, if desired, enzymes effect cleavage of the JC-1 subunit from the toxin or therapeutically useful agent, allowing it to exert the desired effect. Alternatively, the functionalization and covalent attachment of the toxin or therapeutically useful agent does not need to depend on subsequent release of the toxin or therapeutically useful agent by cleavage of the JC-1 subunit from the toxin or therapeutically useful agent, if the attachment point on the toxin or therapeutically useful agent is non-interfering with the function of the active agent within the mitochondria.

FIG. 5 outlines the synthesis of a functionalized "half" JC-1 subunit by several different methods. The attachment of the active chemical species is via the heteroatom incorporated in the JC-1 or "half" JC-1 structure. This attachment may be accomplished by any number of linking strategies such as by taking advantage of a functionality on the active molecule (such as a carboxylic acid to form an ester with the oxygen of the altered JC-1) or by using a linker to space between the JC-1 and the toxin or therapeutically useful agent. These strategies are well known to those skilled in the chemistry of preparing diagnostic or labelling molecules with reporter functions for biological studies and include ester, amide, urethane, urea, sulfonamide, and sulfonate ester (S. T. Smiley et al., *Proc. Nat'l, Acad. Sci. USA,* 88: 3671–3675 (1991)).

As noted hereinabove, mitochondria carrying mutated ATP synthase or tRNA lysine genes have increased levels of cardiolipin and other negatively charged phospholipids as well as increased mitochondrial membrane potential. As a result, the mitochondria selectively accumulate targeting molecules, including acridine orange derivatives and lipophilic cations such as rhodamine-123 and JC-1 derivatives. In addition to selectively introducing toxins or therapeutically useful agents into the mitochondria, such targeting molecules can also selectively introduce imaging ligands, which can form the basis of effective in vivo and in vitro diagnostic strategies. Such strategies include magnetic resonance imaging (MRI), single photon emission computed topography (SPECT), and positron emission tomography (PCT). Preferred imaging ligands for the practice of the present invention include radioisotopes (such as $^{123}$I, $^{125}$I, $^{18}$F, $^{13}$N, $^{15}$O, $^{11}$C, $^{99m}$Tc, $^{67}$Ga and so forth), haptens (such as digoxigenin), biotin, enzymes (such as alkaline phosphatase or horseradish peroxidase), fluorophores (such as fluorescein lanthanide chelates, or Texas Red®), and gadolinium chelates for MRI applications. Saha et al., *Seminars in Nuclear Medicine,* 4: 324–349 (1994).

As an example of an in vitro diagnosis, a targeting molecule, such as an acridine orange or JC-1 derivative, is labelled with fluorescein as an imaging ligand. The labelled targeting molecule is introduced into a human tissue cell culture such as a primary fibroblast culture. After a period of several hours, cells having mitochondria with defective ATP synthase or tRNA lysine genes selectively absorb the labelled targeting molecule in amounts greater than cells without such mitochondria. The cells are then washed and sorted in a fluorescence activated cell sorter (FACS) such as that sold by Becton Dickinson. Threshold limits can be established for the FACS using cells with wild-type mitochondria. Similarly, in an in vivo diagnosis, a targeting molecule such as an acridine orange or JC-1 derivative is labelled with $^{99m}$Tc, $^{18}$F or $^{123}$I as an imaging ligand. This labelled targeting molecule is introduced into the bloodstream of a patient. After a period of several hours, the labelled targeting molecule accumulates in those tissues having mitochondria with mutated ATP synthase or tRNA lysine genes. Such tissues can be directly imaged using positron-sensitive imaging equipment.

Selective destruction of defective mitochondria is also achieved by using ribozymes. Ribozymes are a class of RNA molecules that catalyze strand scission of RNA molecules independent of cellular proteins. Specifically, ribozymes may be directed to hybridize and cleave target mitochondrial mRNA molecules. The cleaved target RNA cannot be translated, thereby preventing synthesis of essential proteins which are critical for mitochondrial function. The therapeutic application thus involves designing a ribozyme which incorporates the catalytic center nucleotides necessary for function and targeting it to mRNA molecules which encode for dysfunctional ATP synthase or tRNA lysine subunits. The ribozymes may be chemically synthesized and delivered to cells or they can be expressed from an expression vector following either permanent or transient transfection. Therapy is thus provided by the selective removal of mutant mRNAs in defective mitochondria.

The foregoing and following description of the invention and the various embodiments is not intended to be limiting of the invention but rather is illustrative thereof. Those skilled in the art of molecular genetics can formulate further embodiments encompassed within the scope of the present invention.

Cybrids

Methods for depleting mitochondrial DNA ("mtDNA") from cells and then transforming those cells with mitochondria from other cells have been reported in the literature. King, M. P. and Attardi, B, *Science* 246: 500–503 (1989). The value of the reported cell lines is limited because they are not of the same type as those cells in which pathogenesis of the disease is expressed. Furthermore, the techniques for mitochondrial transformation of human cells described above allow only limited short term studies. Care has to be taken in growing cultures since transformed, undifferentiated cells containing wild-type mtDNA are healthier than those containing mutant mtDNA and therefore have a propagative advantage in culture. Over the course of several generations, cells with wild-type mtDNA would dominate the cellular population (i.e., mutant mtDNA would be selected against) and cells containing mutated mtDNA would be lost.

The different embodiments of the present invention overcome these two serious limitations. First, using ρ° cells derived from cultures of cell lines in which different cellular manifestations of diabetes mellitus are observed permits analysis of changes in the mitochondrial genome and closely mimics the functional effects of mitochondrial dysfunction in pancreatic β cells and insulin-reponsive cells (e.g., muscle, neurons, adipocytes, etc.). Secondly, by introducing mitochondria from diseased cells into an undifferentiated, immortal cell line, it is possible to maintain the transformants in culture almost indefinitely. Although it would be possible to study and use the undifferentiated cells themselves, it is preferred to take a sample of such cells, and then induce them to differentiate into the cell type that they are destined to become.

Mitochondria to be transferred to construct model systems in accordance with the present invention are isolated from virtually any tissue or cell source. Cell cultures of all types-could potentially be used, as could cells from any tissue. However, cells that are implicated in insulin secretion or that are responsive to insulin, especially isolated pancreatic β cells, fibroblasts, brain tissue, myoblasts, and cell lines derived therefrom are preferred sources of donor mitochondria. Platelets are the most preferred, in part because of their ready abundance, and their lack of nuclear DNA. This preference is not meant to constitute a limitation on the range of cell types that are used as donor sources.

Recipient cells useful to construct models in accordance with the present invention are potentially cells of any type that may be maintained in culture, but immortalized cell lines are preferred because of their growth characteristics. Many such cell lines are commercially available, and new ones are isolated and rendered immortal by methods that are well known in the art. Although cultured cell lines are preferred, it is also possible that cells from another individual, e.g., an unaffected close blood relative, are useful; this could have certain advantages in ruling out non-mitochondrial effects. In any event, it is preferable to use recipient cells that can be induced to differentiate by the addition of particular chemical (e.g., hormones, growth factors, etc.) or physical (e.g., temperature, exposure to radiation such as U.V. radiation, etc.) induction signals.

It is most preferred that the recipient cells be selected such that they are of (or capable of being induced to become) the type that is most phenotypically affected in diseased individuals. For example, for constructing models for mitochondrial defects associated with diabetes, immortalized pancreatic β cell lines are most preferred.

However, the present invention also contemplates that the recipient cell line is a member of the group of cell lines consisting of a mammalian zygote, an embryonic cell capable of differentiating and giving rise to a tissue, an individual, or a germ cell line.

In some embodiments of the present invention mitochondria are transplanted into an immortal, differentiatable cell line, and the transplanted cells are also immortal. The invention further teaches the induction of differentiation among a subpopulation of the immortal culture, which allows for the same experiments to be done as would otherwise have been possible had the transplant been made directly into the differentiated cells. For example, mitochondria from an NIDDM or diabetes mellitus patient are transplanted into an immortalized pancreatic β cell or adipocyte or myoblast or a cell line derived therefrom, subcultures of which are induced to differentiate into pancreatic β cells or fat or muscle cells. The phenotypic expression of the mitochondrial defects in this model system is thus observed in the very cell type that is most affected by the disease.

The only requirement for the method of isolating mitochondria is that the mitochondria be substantially purified from the source cells and that the source cells be sufficiently disrupted that there is little likelihood that the source cells will grow and proliferate in the culture vessels to which the mitochondria are added for transformation. Mitochondrial DNA (mtDNA) of the target cells is removed, for example, by treatment with ethidium bromide. Presumably, this works by interfering with transcription or replication of the mitochondrial genome, and/or by interfering with mRNA translation. The mitochondria are thus rendered unable to replicate and/or produce proteins required for electron transport, and the mitochondria shut down, apparently permanently. However, it is important to note that it is not necessary for the purposes of this invention to use any particular method to remove the mitochondria or mitochondrial DNA.

The cybrid cells of this invention are useful for evaluating chemical compounds for potential utility in the diagnosis or treatment of diabetes mellitus, which encompasses: reducing or delaying the risk of developing diabetes mellitus, and/or treatment of a symptom of diabetes mellitus or a condition that is associated with late onset diabetes mellitus, and/or establishing whether and to what extent a test compound is capable of causing a specified trait to become more similar to those of control cells having mitochondria that lack said defect. This is accomplished by a.) contacting a predetermined quantity of a test compound with cultured cybrid cells having genomic DNA originating from a $\rho^\circ$ cell line and mitochondrial DNA originating from tissue of a human having a disorder that is associated with late onset diabetes mellitus; and b.) measuring a phenotypic trait in said cybrid cells that is affected by said mitochondrial defect; and c.) establishing whether and to what extent said drug is capable of causing said trait to become more similar to those of control cells having mitochondria that lack said defect, which capability indicates that the compound has utility in the treatment of said disorder.

After appropriate clinical tests to determine a safe dosage using methods known in the medical and pharmaceutical arts, the test compounds having utility are administered to humans suffering from or at risk for developing diabetes mellitus. Administration may take place by methods known in the art: e.g., orally, transdermally, by intradermal, intramuscular, subcutaneous, or intravenous injection, etc. Treatment with said compounds will prevent or delay the onset of diabetes mellitus, or will serve to treat at least one symptom of the disease.

Although the present invention is directed primarily towards model systems for diseases in which the mitochondria have metabolic defects, it is not so limited. Conceivably there are disorders wherein there are structural or morphological defects or anomalies, and the model systems of the present invention are of value, for example, to find drugs that address that particular aspect of the disease. In addition, there are certain individuals that have or are suspected of having extraordinarily effective or efficient mitochondrial function, and the model systems of the present invention are of value in studying such mitochondria. In addition, it may be desirable to put known normal mitochondria into cell lines having disease characteristics, in order to rule out the possibility that mitochondrial defects contribute to pathogenesis. All of these and similar uses are within the scope of the present invention, and the use of the phrase "mitochondrial defect" herein should not be construed to exclude such embodiments.

DNA Extraction From Blood Samples

Blood samples (6–7 ml) from 9 NIDDM patients and 6 non-NIDDM (5 controls and 1 Alzheimer's Disease patient) individuals were collected in EDTA Vacutainer tubes. 6 ml of blood was transferred to a 15 ml centrifuge tube and 18 ml of dextran solution (3% dextran, average MW=250,000 kiloDaltons, 0.9% sodium chloride, 1 mM ethylenedinitrilo tetraacetate) was added and mixed. The tube was maintained at room temperature for 40 minutes without agitation to allow erythrocytes to sediment.

The plasma and leukocyte fraction was transferred to a 15 ml centrifuge tube and leukocytes were collected by centrifugation at 14,000 g for 10 minutes. The leukocyte pellet was resuspended in 3.6 ml of water and vortexed for 10 seconds to lyse remaining erythrocytes. 1.2 ml. of 0.6 M sodium chloride was added and the sample was again centrifuged at 14,000 g for 10 minutes to collect the leukocytes. The leukocyte pellet was resuspended in 0.4 ml of a solution containing 0.9% sodium chloride/1 mM EDTA, and stored at −80° C.

Total cellular DNA was isolated from 0.2 ml of the frozen leukocyte sample. The frozen leukocytes were thawed, then collected by centrifugation at 12,000 g in a microcentrifuge for 5 minutes. The cell pellet was washed once with 0.3 ml of Dulbecco's Phosphate Buffered Saline (PBS: Gibco BRL Life Technologies) and resuspended in 0.2 ml water. The leukocytes were lysed by incubating the sample for 10 minutes at 100° C. in a water bath. After the samples were brought to room temperature, cellular debris was pelleted by centrifugation at 14,000 g for 2 minutes. The supernatant was transferred to a clean microcentrifuge tuge. The DNA concentration was determined by UV absorption at 260 nm.

DNA Sequencing

The target tRNA$^{Lys}$ and ATP synthase subunit 8 gene sequences were amplified by polymerase chain reaction (PCR) (Erlich et al., Nature 331:461–462 (1988)). Primers were designed using the published Cambridge sequences for normal human mitochondrial genes. Three primer pairs were designed with sequences homologous to the tRNA$^{Lys}$ gene and the ATP synthase subunit 6 gene (forward and reverse primers (SEQ ID NO:2) and (SEQ ID NO:1), respectively, Table 1), to the cytochrome oxidase subunit 2 gene and the ATP synthase subunit 8 gene (forward and reverse primers (SEQ ID NO:4) and (SEQ ID NO:3) respectively, Table 1), and to the tRNA$^{Lys}$ and the ATP synthase subunit 8 gene (forward and reverse primers (SEQ ID NO:6) and (SEQ ID NO:5), respectively, Table 1).

Primers were chemically synthesized using an ABI 394 DNA/RNA synthesizer (Applied Biosystems Division, Perkin Elmer Corp.) using betacyanoethylphosphoramidite chemistry. The primers were deprotected with ammonium hydroxide and purified using Oligonucleotide Purification Cartridges (ABI, Perkin Elmer Corp.).

TABLE 1

NIDDM: PCR PRIMERS

| PRIMER | PRIMER # | STRAND | LENGTH | POSITION | SEQUENCE 5' -> 3' |
|---|---|---|---|---|---|
| Forward Primer | #1 | L | 23mer | 8292 | GCCCACTGTAAAGCTAACTTAGC |
| Reverse Primer | #1 | H | 22mer | 8631 | TAGTCGGTTGTTGATGAGATAT |
| Forward Primer | #2 | L | 23mer | 8059 | CGTCTTGCACTCATGAGTTGTCC |
| Reverse Primer | #2 | H | 25mer | 8513 | ATTTTCGTTCATTTTGGTTCTCAGG |
| Forward Primer | #3 | L | 25mer | 8311 | TAGCATTAACCTTTTAAGTTAAAGA |
| Reverse Primer | #3 | H | 19mer | 8516 | TCGTTCATTTTGGTTCTCA |

Amplification is performed using 0.5–1.0 µg DNA in a reaction volume of 50–100 µl, containing 10 mM Tris HCl (pH 8.3), 50 mM potassium chloride, 2 mM magnesium chloride, 200 µM each of deoxy-ATP, deoxy-CTP, deoxy-GTP and deoxy-TTP (Amplification cocktail), 200 ng each of the appropriate forward and reverse primers and 5 units of AmpliTaq polymerase (Applied Biosystems Division, Perkin Elmer Corp., Foster City, Calif.; catalogue #N801-0060).

Amplification using primer pairs #1 and #2 was allowed to proceed for one cycle at 95° C. for 10 seconds, 25 cycles at 95° C. for 1 minute, 60° C. for 1 minute, 72° C. for 1 minute, 1 cycle at 72° C. for 4 minutes, after which the samples were cooled to 4° C. Amplification using primer pair #3 was allowed to proceed for one cycle at 95° C. for 10 seconds, 25 cycles at 95° C. for 1 min., 50° C. for 1 min., 72° C. for 1 min., 1 cycle at 72° C. for 4 min., after which the samples were cooled to 4° C. Thermocycling reactions are performed using the GeneAmp PCR system 9600 (Applied Biosystems Division, Perkin Elmer Corp., Foster City, Calif.). Four separate amplification reactions are performed for each DNA sample. After the 4 reactions are complete, the reaction products are pooled for each patient and subunit. The pooled product is precipitated at −80° C. by the addition of 1/10 volume of 5M sodium chloride and 2 volumes of 100% ethanol.

The PCR amplification product is pelleted by centrifugation, dried, resuspended in 40 µl of TE buffer and purified by agarose gel electrophoresis. DNA is stained with ethidium bromide and visualized under long-wavelength ultraviolet light. Bands are excised from the gel, minced and placed into a microcentrifuge tube to which 0.3 ml of 1 M sodium chloride is added. The tube and contents are frozen at −80° C., thawed and incubated at 40° C. for 15–20 minutes. The agarose is sedimented by centrifugation at 14,000 x g for 5 minutes. The supernatant containing the DNA is transferred to a new vial and the DNA is collected by ethanol precipitation.

The amplified DNA is cloned into plasmid pCRII (Invitrogen Corp., San Diego, Calif.) using the TA-cloning Kit (Invitrogen Corp., San Diego, Calif.). Ligations are performed in a reaction volume of 11 μl containing 1–5 μl of PCR amplification product, 2 μl of 10x ligation buffer, and 1 μl of T4 DNA ligase(4 units). Ligation reactions are incubated at 10–12° C. for 15–16 hours.

Vector-ligated PCR fragments are transformed into competent E. coli cells of the strain XL1-Blue MRF' (Stratagene, San Diego, Calif.). Transformed cells are spread into LB-agar plates containing ampicillin (50 mg/ml), kanamycin (50 mg/ml), isopropyl-β-D-thiogalactopyranoside (20 μg/ml), and X-Gal (100 μg/ml). The blue/white color selection provided by the cloning vector allows for easy detection of recombinant clones (i.e., white stained clones).

Plasmid DNA containing gene inserts is isolated using the Qiawell 96 Plasmid Purification Kit (Qiagen, Chatsworth, Calif.). Plasmid DNA is purified from 5 ml bacterial cultures. The isolated DNA is resuspended in 100 μl TE buffer. The DNA is quantitated by $A_{260}$ absorbance of a 1:50 dilution.

Sequencing reactions using double stranded plasmid DNA are performed using the Prism™ Ready Reaction DyeDeoxy™ Terminator Cycle Sequencing Kit (Applied Biosystems Division, Perkin Elmer Corp., Foster City, Calif.). The DNA sequences are detected by fluorescence using the ABI 373A Automated DNA Sequencer (Applied Biosystems Division, Perkin Elmer Corp., Foster City, Calif.). Oligonucleotide primers are synthesized on the ABI 394 DNA/RNA Synthesizer using standard beta-cyanoethylphosphoramidite chemistry. The following primer sequences were synthesized: M13(−20) forward prime and M13 reverse primer.

Sequence data were analyzed by comparison with the published Cambridge sequences. Mutations for each individual were compiled as summarized in Table 2.

Sequencing reactions were performed according to the manufacturer's instructions. Electrophoresis and sequence analysis are performed using the ABI 373A Data Collection and Analysis Software and the Sequence Navigator Software (Applied Biosystems Division, Perkin Elmer Corp., Foster City, Calif.). Sequencing gels were prepared according to the manufacturer's specifications. An average of ten different clones from each individual was sequenced. The resulting ATP synthase 8 and tRNA lysine sequences were aligned and compared with the published sequence. Differences in the derived sequence from the published sequence are noted and confirmed by sequence of the complementary DNA strand.

The open reading frame of the mitochondrial gene for ATP Synthase Subunit 8 includes nucleotide positions 8366 to 8572. The open reading frame of the mitochondrial gene for ATP Synthase subunit 6 ranges from nucleotide position 8527–9207 including overlapping sequence with the ATP Synthase subunit 8 gene (nucleotide positions 8527–9207). The gene for the tRNA Lysine, which includes nucleotide positions 8295 to 8364, is located directly upstream of the ATP synthase gene.

Clonal analysis of the mitochondrial tRNA lysine gene and ATP synthase 8/6 gene revealed quantitative differences in the levels of heteroplasmy at specific nucleotide positions in these two genes between patients with non-insulin dependent diabetes and controls.

Table 2 shows sequence data using primer pair #1 and #2 (Table 1) for prior amplification for each of the 15 subjects. Mutational burden at each specific nucleotide position is indicated as percentage of mutated clones for total quantity of clones sequenced.

Eight base changes were found in the $tRNA^{Lys}$ gene (Table 2). The level of heteroplasmy at each of these nucleotide positions was elevated in most NIDDM patients. Two of the six controls also had modest levels of heteroplasmy at several nucleotide positions.

Twelve nucleotide changes that lead to amino acid changes (missense mutations) were noted in the ATP synthase 8/6 gene. An additional 26 nucleotide changes were seen in the ATP synthase 8/6 gene (Table 2). These additional mutations do not lead to amino acid changes and thus are considered silent mutations. The level of heteroplasmy at each of these nucleotide positions was elevated in most NIDDM patients. Again, two of the six controls also had modest levels of heteroplasmy at some nucleotide positions.

In general, the levels of heteroplasmy at each of these nucleotide sites in these two genes was increased above the controls levels in most patients with NIDDM. For example, the level of heteroplasmy at nucleotide position 8401 varies from 16 to 47% in NIDDM patients and from 0 to 20% in controls. The two controls exhibiting heteroplasmy above 15% may be presymptomatic individuals who are at risk for developing NIDDM. Levels of heteroplasmy above 16% at these specific nucleotide positions may indicate the presence of or risk of developing diabetes mellitus.

TABLE 2

Mutational Analysis: tRNA Lysine and ATP Synthase Subunits 8/6 tRNA Lysine / ATP Synthase Subunit 8

| NUCLEOTIDE # | 8305 | 8310 | 8336 | 8338 | 8345 | 8348 | 8349 | 8351 | 8371 | 8374 | 8383 | 8386 | 8392 | 8395 | 8396 | 8398 | 8401 | 8404 | 8410 | 8419 | 8422 | 8423 | 8428 | 8450 |
|---|---|---|---|---|---|---|---|---|---|---|---|---|---|---|---|---|---|---|---|---|---|---|---|---|
| AMINO ACID WT | N/A | N/A | N/A | N/A | N/A | N/A | N/A | N/A | Pro | Gln | Thr | Thr | Trp | Pro | Thr | Thr | Met | Ile | Pro | Leu | Thr | Leu | Phe | Leu |
| AMINO ACID MT | N/A | N/A | N/A | N/A | N/A | N/A | N/A | N/A | Pro | Gln | Thr | Thr | Trp | Pro | Ala | Thr | Ile | Ile | Pro | Leu | Thr | Leu | Phe | Leu |
| NUCLEOTIDE WT | C | T | T | A | C | A | C | C | C | A | T | C | G | C | A | C | A | A | C | C | A | C | C | T |
| NUCLEOTIDE MT | T | C | C | G | T | C | T | T | A | G | C | T | A | T | G | T | C | T | A | T | G | T | T | C |
| PATIENT AG # DIAGNOSIS |||||||||||||||||||||||||
| EO 289 NIDDM | 0 | 0 | 33 | 0 | 33 | 33 | 33 | 33 | 33 | 33 | 33 | 33 | 33 | 33 | 33 | 33 | 33 | 33 | 33 | 33 | 33 | 33 | 33 | 33 |
| EP 293 NIDDM | 0 | 0 | 20 | 0 | 20 | 20 | 20 | 20 | 20 | 20 | 20 | 20 | 20 | 20 | 20 | 20 | 20 | 20 | 20 | 20 | 20 | 20 | 20 | 20 |
| FA 306 NIDDM | 0 | 0 | 33 | 0 | 33 | 33 | 33 | 33 | 33 | 33 | 33 | 33 | 33 | 33 | 33 | 33 | 33 | 33 | 33 | 33 | 33 | 33 | 33 | 33 |
| EL 283 NIDDM | 8 | 8 | 40 | 7 | 47 | 47 | 47 | 40 | 47 | 47 | 47 | 47 | 47 | 40 | 40 | 40 | 47 | 40 | 47 | 47 | 40 | 40 | 47 | 40 |
| ER 300 NIDDM | 9 | 9 | 20 | 0 | 20 | 20 | 20 | 20 | 20 | 20 | 20 | 20 | 20 | 20 | 20 | 20 | 20 | 20 | 20 | 20 | 20 | 20 | 20 | 20 |
| 469 469 NIDDM | 12 | 12 | 17 | 4 | 21 | 21 | 16 | 17 | 16 | 20 | 16 | 16 | 16 | 14 | 17 | 14 | 16 | 14 | 16 | 21 | 14 | 17 | 16 | 17 |
| 578 578 NIDDM | 15 | 15 | 14 | 2 | 16 | 20 | 20 | 14 | 20 | 20 | 20 | 20 | 16 | 14 | 14 | 14 | 20 | 14 | 20 | 20 | 14 | 14 | 20 | 14 |
| 733 733 NIDDM | 25 | 25 | 4 | 16 | 20 | 20 | 20 | 4 | 20 | 20 | 20 | 20 | 20 | 20 | 14 | 4 | 20 | 4 | 20 | 20 | 4 | 4 | 20 | 4 |
| 909 909 NIDDM | 8 | 8 | 6 | 17 | 23 | 23 | 23 | 6 | 23 | 23 | 23 | 23 | 23 | 23 | 6 | 6 | 23 | 6 | 23 | 23 | 6 | 6 | 23 | 6 |
| KJ 294 CONTROL | 10 | 10 | 10 | 0 | 10 | 10 | 10 | 10 | 10 | 10 | 10 | 10 | 10 | 10 | 10 | 10 | 10 | 10 | 10 | 10 | 10 | 10 | 10 | 10 |
| PS 314 CONTROL | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| GM 50 CONTROL | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| FB331 331 AD | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| GA 27 CONTROL | 18 | 18 | 2 | 18 | 20 | 20 | 20 | 2 | 20 | 20 | 20 | 20 | 20 | 20 | 2 | 2 | 20 | 2 | 20 | 20 | 2 | 2 | 20 | 20 |
| SH 25 CONTROL | 10 | 10 | 8 | 10 | 18 | 18 | 18 | 8 | 18 | 18 | 18 | 18 | 18 | 18 | 8 | 8 | 18 | 8 | 18 | 18 | 8 | 8 | 18 | 18 |

ATP Synthase Subunit 8 / ATP Synthase 8/6

| NUCLEOTIDE # | 8459 | 8463 | 8467 | 8470 | 8473 | 8474 | 8485 | 8486 | 8487 | 8488 | 8491 | 8503 | 8506 | 8508 | 8509 | 8512 | 8539 | 8541 | 8557 | 8562 | 8566 | 8568 |
|---|---|---|---|---|---|---|---|---|---|---|---|---|---|---|---|---|---|---|---|---|---|---|
| AMINO ACID WT | Asn | Tyr | His | Leu | Pro | Pro | Lys | Pro | Pro | Pro | Met | Asn | Tyr | Asn | Asn | Lys | Ile | Cys | Leu | Pro | Gln | Ser |
| AMINO ACID MT | Asp | Cys | His | Leu | Pro | Thr | Lys | Ser | Leu | Pro | Ile | Asn | Tyr | Ser | Asn | Lys | Ile | Tyr | Leu | Leu | Gln | Tyr |
| NUCLEOTIDE WT | A | A | C | A | T | C | G | C | C | C | A | T | T | A | C | A | A | G | G | C | A | C |
| NUCLEOTIDE MT | G | G | T | G | C | A | A | T | T | T | T | C | C | G | T | G | T | A | A | T | G | A |
| PATIENT AG # DIAGNOSIS |||||||||||||||||||||||
| EO 289 NIDDM | 33 | 33 | 33 | 33 | 33 | 33 | 33 | 33 | 33 | 33 | 33 | 33 | 33 | 33 | 33 | 33 | 33 | 40 | 33 | 40 | 33 | 33 |
| EP 293 NIDDM | 20 | 20 | 20 | 20 | 20 | 20 | 20 | 20 | 20 | 20 | 20 | 20 | 20 | 20 | 20 | 20 | 20 | 33 | 20 | 33 | 20 | 20 |
| FA 306 NIDDM | 33 | 33 | 33 | 33 | 33 | 33 | 33 | 33 | 33 | 33 | 33 | 33 | 33 | 33 | 33 | 33 | 33 | 33 | 33 | 33 | 33 | 33 |

TABLE 2-continued

Mutational Analysis: tRNA Lysine and ATP Synthase Subunits 8/6

| | | | | | | | | | | | | | | | | | |
|---|---|---|---|---|---|---|---|---|---|---|---|---|---|---|---|---|---|
| EL | 283 | NIDDM | 40 | 40 | 40 | 47 | 40 | 47 | 40 | 47 | 40 | 47 | 40 | 47 | 40 | 47 | 40 |
| ER | 300 | NIDDM | 20 | 20 | 20 | 20 | 20 | 20 | 20 | 20 | 20 | 20 | 20 | 20 | 20 | 20 | 20 |
| 469 | 469 | NIDDM | 17 | 17 | 17 | 21 | 17 | 21 | 17 | 21 | 17 | 21 | 17 | 21 | 17 | 21 | 17 |
| 578 | 578 | NIDDM | 14 | 14 | 14 | 16 | 14 | 16 | 14 | 16 | 14 | 16 | 14 | 16 | 14 | 16 | 14 |
| 733 | 733 | NIDDM | 4 | 4 | 4 | 20 | 4 | 20 | 4 | 20 | 4 | 20 | 4 | 20 | 4 | 20 | 4 |
| 909 | 909 | NIDDM | 6 | 6 | 6 | 23 | 6 | 23 | 6 | 23 | 6 | 23 | 6 | 23 | 6 | 23 | 6 |
| KJ | 294 | CONTROL | 10 | 10 | 10 | 10 | 10 | 10 | 10 | 10 | 10 | 10 | 10 | 10 | 10 | 10 | 10 |
| PS | 314 | CONTROL | 0 | 0 | 0 | 0 | 0 | 0 | 0 | 0 | 0 | 0 | 0 | 0 | 0 | 0 | 0 |
| GM | 50 | CONTROL | 0 | 0 | 0 | 0 | 0 | 0 | 0 | 0 | 0 | 0 | 0 | 0 | 0 | 0 | 0 |
| FB331 | 331 | AD | 2 | 2 | 2 | 20 | 2 | 20 | 2 | 20 | 2 | 20 | 2 | 20 | 2 | 20 | 2 |
| GA | 27 | CONTROL | 8 | 8 | 8 | 18 | 8 | 18 | 8 | 18 | 8 | 18 | 8 | 18 | 8 | 18 | 8 |
| SH | 25 | CONTROL | | | | | | | | | | | | | | | |

☐ Silent Mutation
■ Missense Mutation
▦ tRNA Mutation

Synthesis of Antisense Oligonucleotides

Standard manufacturer protocols for solid phase phosphoramidite-based DNA or RNA synthesis using an ABI DNA synthesizer are employed to prepare antisense oligomers. Phosphoroamidite reagent monomers (T, C, A, G, and U) are used as received from the supplier. Applied Biosystems Division/Perkin Elmer, Foster City, Calif. For routine oligomer synthesis, 1 µmole scale synthesis reactions are carried out utilizing THF/$I_2$/lutidine for oxidation of the phosphoramidite and Beaucage reagent for preparation of the phosphorothioate oligomers. Cleavage from the solid support and deprotection are carried out using ammonium hydroxide under standard conditions. Purification is carried out via reverse phase HPLC and quantification and identification is performed by UV absorption measurements at 260 nm, and mass spectrometry.

Inhibition of Mutant Mitochondria in Cell Culture

Antisense phosphorothiodate oligomer complementary to the ATP synthase and tRNA lysine gene mutants and thus non-complementary to wild-type ATP synthase or tRNA lysine gene are added to fresh medium containing Lipofectin® Gibco BRL (Gaithersburg, Md.) at a concentration of 10 µg/ml to make final concentrations of 0.1, 0.33, 1, 3.3, and 10 µM. These are incubated for 15 minutes then applied to the cell culture. The culture is allowed to incubate for 24 hours and the cells are harvested and the DNA isolated and sequenced as in previous examples. Quantitative analysis results shows a decrease in mutant ATP synthase or tRNA lysine DNA to a level of less than 1% of total ATP synthase or tRNA lysine wild-type DNA.

The antisense phosphorothioate oligomer complementary to these genes and non-complementary to wild-type gene is added to fresh medium containing lipofectin at a concentration of 10 µg/ml to make final concentrations of 0.1, 0.33, 1, 3.3, and 10 µM these are incubated for 15 minutes then applied to the cell culture. The culture is allowed to incubate for 24 hours and the cells are harvested and the DNA isolated and sequenced as in previous examples. Quantitative analysis results showed no decrease in mutant COX DNA.

Inhibition of Mutant Mitochondria in Vivo

Mice are divided into six groups of 10 animals per group. The animals are housed and fed as per standard protocols. Antisense phosphorothioate oligonucleotide complementary to mutant ATP synthase gene RNA, prepared as described above, is administered intramuscularly (I.M.) to groups 1 to 4, in the following amount: 0.1, 0.33, 1.0 and 3.3 nmol each in 5 µL. To group 5 is administered I.M. 1.0 nmol in 5 µL of phosphorothioate oligonucleotide non-complementary to mutant ATP synthase gene RNA and non-complementary to wild-type ATP synthase gene RNA. To group 6 is administered I.M. vehicle only. Dosing is performed once a day for ten days. The animals are sacrificed and samples of muscle and pancrease collected. This tissue is treated as previously described and the DNA isolated and quantitatively analyzed as in previous examples. Results show a decrease in mutant ATP synthase DNA to a level of less than 1% of total ATP synthase for the antisense treated group and no decrease for the control group.

Agents for the Detection and Selective Destruction of Defective Mitochondria a. Preparation of 10-N-(10-Hydroxy-1-decyl)-3,6 bis (dimethylamino)acridine bromide salt 3,6-bis(dimethylamino)acridine (1.0 millimole) is dissolved in DMF (100 ml) containing 1.1 equivalent of tertiary amine base. To this is added 10-hydroxy-1-bromo decane (1.1 millimole), and the mixture is heated to reflux. When monitoring by TLC shows no remaining 3,6-bis (dimethylamino)acridine, the reaction is cooled and the 10-N-(10-hydroxy-1-decyl)-3,6-bis(dimethylamino) acridine is isolated (0.75 millimoles).

b. Preparation of 10-N-(10-phosphoryl-1-decyl)-3,6-bis (dimethylamino)acridine chloride salt 10-N-(10-Hydroxy-1-decyl)-3,6-bis(dimethylamino) acridine (1.0 millimole) is dissolved in pyridine (100 ml). To this is added 2-(N,N-dimethylamino)-4-nitrophenyl phosphate (1.1 millimole) according to the procedure of Taguchi (*Chem. Pharm. Bull.*, 23: 1586 (1975), and the mixture is stirred under a nitrogen atmosphere. When monitoring by TLC showed no remaining 10-N-(10-hydroxy-1-decyl)-3,6-bis(dimethylamino)acridine, the reaction is worked up according to Taguchi and the 10-N-(10-phosphoryl-1-decyl)-3,6-bis(dimethylamino)acridine is isolated (0.75 millimoles).

c. Preparation of 10-N-(10-thiophosphoryl-1-decyl)-3,6-bis (dimethylamino)acridine chloride salt 10-N-(10-hydroxy-1-decyl)-3,6-bis(dimethylamino) acridine (1.0 millimole) is dissolved in DMF (100 ml). To this is added triimidazolyl-1-phosphine sulfide (1.1 millimole) according to the procedure of Eckstein (*Journal of the American Chemical Society*, 92: 4718, (1970)) and the mixture stirred under a nitrogen atmosphere. When monitoring by TLC shows no remaining 10-N-(10-Hydroxy-1-decyl)-3,6-bis(dimethylamino)acridine, the reaction is worked up according to Eckstein and the 10-N-(10-thiophosphoryl-1-decyl)-3,6-bis(dimethylamino)acridine is isolated (0.75 millimoles).

d. Preparation of 10-N-(11-undecanoic acid)-3,6-bis (dimethylamino)acridine bromide salt 3,6-Bis(dimethylamino)acridine (1.0 millimole) is dissolved in DMF (100 ml). To this is added 11-bromo undecanoic acid (1.1 millimole) and the mixture is heated to reflux. When monitoring by TLC shows no remaining 3,6-bis(dimethylamino)acridine, the reaction is cooled and the 10-N-(11-undecanoic acid)-3,6-bis(dimethylamino) acridine is isolated (0.75 millimoles).

e. Preparation of 10-N-(11-undecyl-2,4-dinitrophenyl urethane)-3,6-bis(dimethylamino)acridine bromide salt 10-N-(11-Undecanoic acid)-3,6-bis(dimethylamino) acridine (1.0 millimole) is dissolved in DMF (100 ml). To this is added 2,4-dinitrophenol (1.1 millimole) and diphenylphosphoryl azide (1.1 millimole), and the mixture is stirred while heating to 70° C. When monitoring by TLC shows no remaining 10-N-(11-undecanoic acid)-3,6-bis (dimethylamino)-acridine, the reaction is cooled and the 10-N-(11-undecyl-2,4-dinitrophenyl urethane)-3,6-bis (dimethylamino)acridine is isolated (0.75 millimoles).

f. Preparation of 10-N-(11-undecan-1-oic acid 2,4-dinitrophenyl ester)-3,6-bis(dimethylamino)acridine bromide salt 10-N-(11-undecanoic acid)-3,6-bis(dimethylamino) acridine (1.0 millimole) is dissolved in DMF (100 ml). To this is added 2,4-dinitrophenol (1.1 millimole), dicyclohexylcarbodimide (1.1 millimole) and hydroxybenztriazole (1.1 millimole), and the mixture is stirred. When monitoring by TLC shows no remaining 10-N-(11-undecanoic acid)-3,6-bis(dimethylamino)-acridine, the reaction is cooled and the 10-N-(11-undecan-1-oic acid 2,4-dintrophenyl ester)-3,6-bis(dimethylamino)acridine is isolated (0.75 millimoles).

g. Preparation of N'-(2-hydroxyethyl)-JC-1

According to the procedure of Yamamoto et al. *Bulletin of the Chemical Society of Japan,* 46: 1509–11 (1973)), 2-methyl-5,6-dichloro-N-ethyl-N'-(2-hydroxyethyl) benzimidazole is heated with aniline and ethyl orthoformate at 100° C. To this is added acetic anhydride and potassium acetate and heating is continued at 160° C. The reaction is worked up as described in Yamamoto et al. and the product isolated.

h. Preparation of bis N'-(2-phosphoryl-1-ethyl)-JC-1

N'-(2-hydroxyethyl)-JC-1 (1.0 millimole) is dissolved in pyridine (100 ml). To this is added 2-(N,N-dimethylamino)-4-nitrophenyl phosphate (1.1 millimole) according to the procedure of Taguchi, *Chem. Pharm. Bull.,* 23, 1586 (1975), and the mixture is stirred under a nitrogen atmosphere. When monitoring by TLC shows no remaining 10-N-(10-hydroxy-1-decyl)-3,6-bis(dimethylamino)acridine, the reaction is worked up according to Taguchi and bis N'-(2-phosphoryl-1-ethyl) JC-1 was isolated (0.75 millimoles).

Although the invention has been described with reference to the above-provided examples, it should be understood that various modifications can be made without departing from the spirit of the invention.

What is claimed is:

1. A cybrid cell line, comprising: cultured cells having genomic and mitochondrial nucleic acids of different biological origins, wherein said mitochondrial or genomic nucleic acid is derived from an individual exhibiting symptoms of late onset diabetes mellitus or at risk for developing symptoms for late onset diabetes mellitus.

2. The cybrid cell line of claim 1 wherein said cybrid is made by:

a) treating a parental cell or cell line with a chemical agent capable of converting said cell or cell line into a $\rho°$ cell line; and b) transfecting said $\rho°$ cell line with isolated mitochondria to form said cybrid cell line.

3. The cybrid of claim 2, wherein said parental cell or cell line is undifferentiated, but capable of being induced to differentiate.

4. The cybrid of claim 2, wherein said cybrid cell line is immortal.

5. The cybrid of claim 4, wherein said cybrid cell line is undifferentiated, but capable of being induced to differentiate.

6. A cybrid cell line according to claim 2, wherein the parental cell or cell line is selected from the group consisting of: a zygote, an embryonic cell capable of differentiating and giving rise to a tissue or an individual, a germ cell line, pancreatic $\beta$ cell or cell line, fat cell or cell line, muscle cell or cell line, and an insulin-responsive cell other than a pancreatic $\beta$ cell line, a fat cell, and muscle cell.

* * * * *

UNITED STATES PATENT AND TRADEMARK OFFICE
CERTIFICATE OF CORRECTION

PATENT NO : 6,146,831
DATED : Nov. 14, 2000
INVENTOR(S) : Davis et al.

It is certified that errors appear in the above-identified patent and that said Letters Patent are hereby corrected as shown below:

Section [60], Related U.S. Application Data, on the front cover, "No. 08/732,564" is incorrect and should read --No. 08/734,564--.

Claim 2, column 35, line 46, "claim 1 wherein" is incorrect and should read --claim 1, wherein--.

Signed and Sealed this

First Day of May, 2001

Attest:

NICHOLAS P. GODICI

*Attesting Officer*  *Acting Director of the United States Patent and Trademark Office*